United States Patent

Dushin et al.

Patent Number: 5,932,745
Date of Patent: Aug. 3, 1999

[54] PROCESS FOR CONVERTING PROPARGYLIC AMINE-N-OXIDES TO ENAMINONES

[75] Inventors: Russell G. Dushin, Putnam, N.Y.; Eugene J. Trybulski, Princeton Junction, N.J.

[73] Assignee: American Home Products Corporation, Madison, N.J.

[21] Appl. No.: 09/106,471

[22] Filed: Jun. 30, 1998

Related U.S. Application Data

[60] Provisional application No. 60/054,251, Jul. 30, 1997.

[51] Int. Cl.$^6$ ............ C07D 207/12; C07D 205/04; C07D 203/08; C07D 401/06
[52] U.S. Cl. ............ 548/540; 548/950; 548/964; 548/967; 548/579; 546/208; 546/246; 544/162
[58] Field of Search ............ 546/208, 246; 548/540

[56] References Cited

U.S. PATENT DOCUMENTS

| | | | |
|---|---|---|---|
| 4,937,235 | 6/1990 | Trybulski et al. | 514/63 |
| 5,059,709 | 10/1991 | Dusza et al. | 558/309 |
| 5,550,257 | 8/1996 | Trybulski et al. | 548/550 |

OTHER PUBLICATIONS

Hallstrom et al., Decomposition of Prop–2–ynylic N Oxides . . . , Tetrahedron Letters, vol. 21, pp. 667–670, Dec. 1980.
Greenhill, J.V. *Chem. Soc. Rev.* 1977, 6, 277.
Mannich, C., et al., *Chem Ber.* 1933, 66, 418.
Sanogashira, et al. *Tetrahedron Lett.* 1975, 4467 Unroe, M.R., et al. *Synthesis* 1978, 981.
Unroe, M.R., et al. *Synthesis* 1978, 981.
Stille, J.K. *Angew. Chem. Intl. Ed. Engl.* 1986, 25, 508.
Scott, W.J. et al. *Acc. Chem. Res.* 1988, 21, 47.
Kalinin, V.N. *Synthesis* 1992, 413.
Ritter, K. *Synthesis* 1993, 735.
Albini, A. *Synthesis* 1993, 263.
Murray, R.W. *Chem. Rev.* 1989, 1187.
Torregrosa, J.L. et al. *Tetrahedron* 1982, 38, 2355.
McMullen, C.H. et al. *J. Chem Soc.* 1966, 1217.
Hales, N.J. et al. *Tetrahedron* 1995, 51, 7403.
Ligouri, A. et al. *Tetrahedron* 1988, 44, 1255.
Craig, J.C. et al. *Tetrahedron Lett.* 1979, 4025.
Hallström, G. et al. *Tetrahedron Lett.* 1980, 21, 667.
Khuthier, A–H. et al. *J. Chem. Soc. Chem. Comm.* 1979, 9.
Weizmann, *J. Amer. Chem. Soc.* 1949, 71, 4154.
Hirao, I. *J. Chem. Soc. Japan* 1953, 968.
Neale, R.S. et al. *J. Org. Chem.* 1964, 29, 3390.
Katritzky, A.R. et al. *Synthesis* 1989, 949.
Clarke, H.T. et al. *Organic Synthesis, vol. I* 1941, 514.
Kucklaender, U. "Enaminones as Synthons", in *Chemistry of Enamines*, Rappoport, Ed., vol. 1, pp. 523–636, Chichester, UK: Wiley [1994].
Craig et al., J. Org. Chem., vol. 35, No. 5., May 1970, pp. 1721–1722.

*Primary Examiner*—Johann Richter
*Assistant Examiner*—Dominic Keating
*Attorney, Agent, or Firm*—Steven R. Eck

[57] ABSTRACT

This invention concerns the use of a hydroxylic solvent in the preparation of enaminones from the corresponding amine N-oxides or propargylic amines via the general process outlined below:

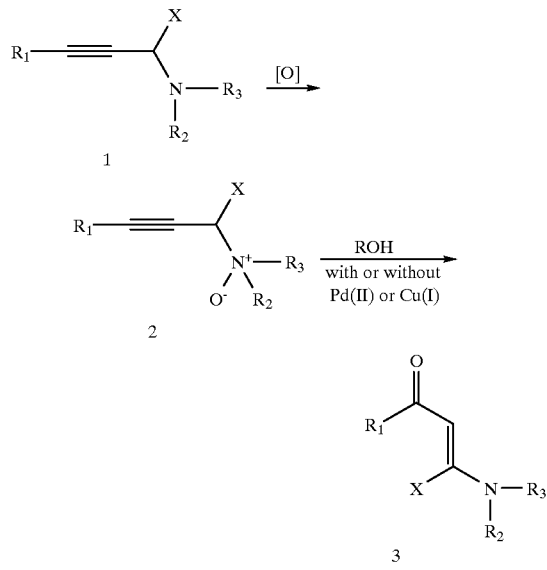

26 Claims, No Drawings

PROCESS FOR CONVERTING PROPARGYLIC AMINE-N-OXIDES TO ENAMINONES

This application claims the benefit of U.S. provisional application Ser. No. 60/054,251, filed Jul. 30, 1997.

This invention relates to a process for the production of enaminones from propargylic amine N-oxides. More particularly, this invention relates to a process for preparing amine N-oxides from corresponding propargylic ammines using conventional oxidative methods and forming enaminones from the amine N-oxides by exposure to hydroxylic solvents in the presence or absence of metal catalysts with or without heating.

BACKGROUND OF THE INVENTION

Enaminones are versatile synthetic intermediates that are easily converted into a wide variety of functional groups, including (but not limited to) β-aminoketones, β-hydroxyketones, alkyl-substituted enones, and numerous heterocycles including isoxazoles, pyrazoles, pyrimidines, pyridines and thiophenes. Enaminones are of times used in the production of compounds of commercial importance (pharmaceuticals, insecticides, dyestuffs, etc.).

Enaminones can be synthesized by a variety of methods including the reaction of an amine with a 1,3-diketone, a 3-keto ester, a vinylogous ester, a vinylogous acid chloride, a β-dialkoxy ketone, a β-cyanovinyl ketone, an acetylenic ketone, by the condensation of a ketone with N,N-dimethylformamide acetal, by the acylation of enamines, by reaction of ketene with enamines, by reaction of oxime sulfonates with silyl enol ethers, by the palladium assisted amination of an olefin, by the palladium catalyzed dehydrogenation of a β-amino ketone, or by the Mannich reaction of a ketone with a secondary amine and an orthoester. The preparation and use of enaminones has been the subject of two reviews: Greenhill, J. V. *Chem. Soc. Rev.* 1977, 6, 277; Kucklaender, U. "Enaminones as Synthons", in *Chemistry of Enamines*, Rappoport, Ed., Vol. 1, pp. 523–636, Chichester, UK: Wiley [1994].

Functionalized propargylic amines can be conveniently prepared by the copper-catalyzed Mannich reaction of terminal acetylenes with formaldehyde and amines (Mannich, *Chem. Ber.* 1933, 66, 418) or, in the case of 3-aryl or 3-vinyl substituted prop-2-ynyl amines, by palladium-catalyzed couplings of 1-amino-prop-2-ynes with aryl or vinyl halides or triflates (Sanogashira, et.al. *Tetrahedron lett.* 1975, 4467; Unroe, et.al. *Synthesis* 1987, 981; Stille, J. K. *Angew. Chem., Intl. Ed. Engl.* 1986, 25, 508; Scott, et.al. *Acc. Chem. Res.* 1988, 21, 47; Kalinin, V. N. *Synthesis* 1992, 413; Ritter,K. *Synthesis* 1993, 735). These amines can be easily converted into the respective amine N-oxides by any of a number of standard oxidative procedures (as discussed in Albini, A. *Synthesis* 1993, 263) or with dioxirane reagents (reviewed in Murray, R. W. *Chem. Rev.* 1989, 1187).

Although the precise mechanism by which a propargylic amine N-oxide is converted into an enaminone product has not been rigorously determined, it likely resembles two known processes; the thermal [2,3]-sigmatropic rearrangement of propargylic amine N-oxides and the conversion of certain isoxazoles into enaminones. A proposed mechanism is shown below:

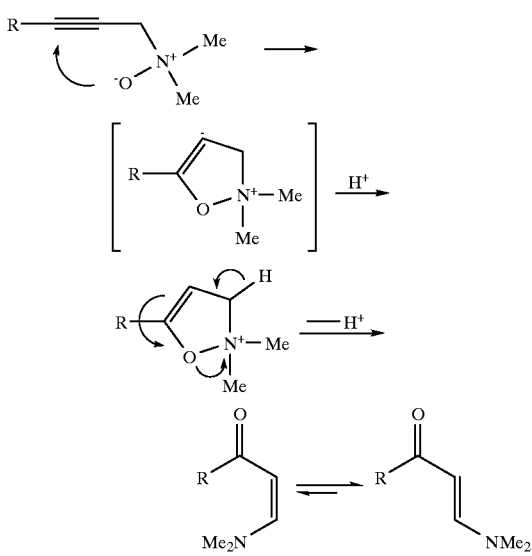

The thermal conversion by [2,3]-sigmatropic rearrangement of propargylic amine N-oxides to hydroxyl amine O-allenyl ethers is a known reaction (Equation 1, below; Craig, et.al. *Tetrahedron Lett.* 1979, 4025; Hallstrom, et.al. *Tetrahedron Lett.* 1980, 667; Khuthier, A-H, et.al. *J. Chem. Soc. Chem. Commun.* 1979, 9). In each instance where this [2,3]-sigmatropic rearrangement has been reported, the reactions were performed either neat or in aprotic solvents (e.g. dimethylformamide, diethyl ether, tetrahydrofuran, carbon tetrachloride) and the formation of enaminone products has not been disclosed.

Equation 1.

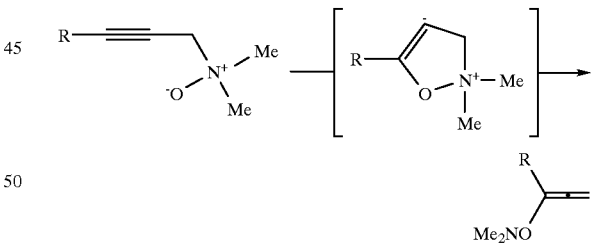

Substituted enaminones can result from the hydrolytic breakdown of certain substituted isoxazolines (Equation 2, below), as described by Liguori, et.al. *Tetrahedron* 1988, 44, 1255. The isoxazolines of Liguori et al. were prepared by the 1,3-dipolar cycloaddition reaction of C-benzoyl-N-phenylnitrone with alkynes (formed as a mixture with its regioisomer). It appears that the substitution pattern about the isoxazoline ring influences the outcome of this hydrolytic reaction. This process is an isolated example of enaminone formation from isoxazolines and is not a generally applicable nor synthetically useful transformation.

Equation 2.

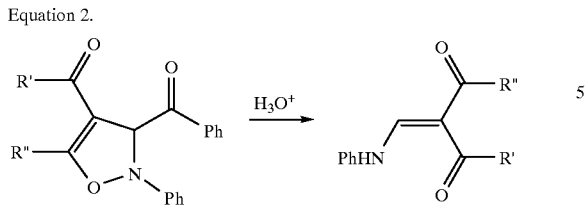

The present invention provides a novel synthesis of enaminones from propargylic amine N-oxides upon exposure to hydroxylic solvents. This new method of enaminone synthesis provides a convenient alternative to existing methods and further extends the range of starting materials that can be converted into enaminone products.

SUMMARY OF THE INVENTION

This invention provides a novel process for the synthesis of enaminones of Formula (I):

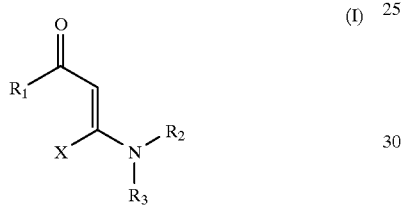
(I)

wherein:

X is selected from the group of H, $C_1$–$C_6$ straight chain alkyl, $C_3$–$C_6$ branched chain alkyl, $C_3$–$C_7$ cycloalkyl, —$CH_2$-phenyl, or —$CH_2$-substituted phenyl;

$R_1$ is selected from the group of hydrogen, $C_1$–$C_6$ straight chain alkyl, $C_3$–$C_6$ branched chain alkyl, $C_3$–$C_7$ cycloalkyl, phenyl, substituted phenyl, —$CH_2$-phenyl, or —$CH_2$-substituted phenyl or a group of the formulae:

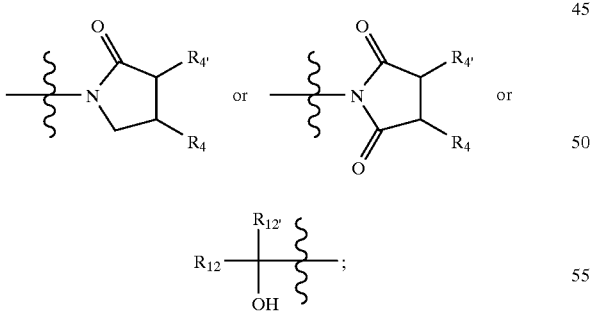

the $C_3$–$C_7$ cycloalkyl groups being optionally substituted by from 1 to 3 groups independently selected from $R_5$–$R_9$;

$R_2$ and $R_3$ are independently selected from the group of $C_1$–$C_6$ straight chain alky, $C_3$–$C_6$ branched chain alkyl, $C_3$–$C_7$ cycloalkyl, or —$CH_2$-phenyl;

$R_2$ and $R_3$ may also be joined to form a ring of from three to six atoms. Thus, for example, cyclic versions of —$NR_2R_3$ include, but are not limited to, the following:

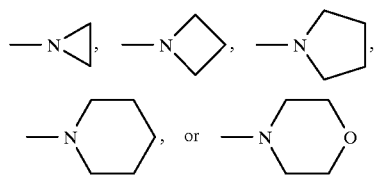

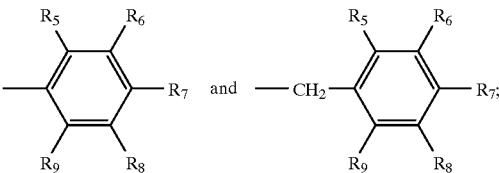

$R_4$ and $R_{4'}$ are independently selected from the group of hydrogen, $C_1$–$C_6$ straight chain alkyl, $C_3$–$C_6$ branched chain alkyl, $C_3$–$C_7$ cycloalkyl, —$OR_{11}$, —$NR_{11}R_{13}$, —$NR_{11}C(O)OR_{10}$, —$NR_{11}C(O)R_{10}$, —$OC(O)R_{10}$, —$OC(O)OR_{10}$, or —$OC(O)NHR_{10}$;

Substituted phenyl and —$CH_2$-substituted phenyl are, respectively:

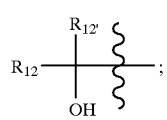

$R_5$–$R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)OR_{11}$, —$NR_{11}C(O)R_{11}$, —$OC(O)R_{11}$, —$OC(O)OR_{11}$, or —$OC(O)NHR_{11}$;

$R_{10}$ is selected from the group of hydrogen, $C_1$–$C_{10}$ straight chain alkyl, $C_3$–$C_{10}$ branched chain alkyl, $C_3$–$C_7$ cycloalkyl, phenyl, or —$CH_2$-phenyl;

$R_{11}$ and $R_{11'}$ are independently selected from the group of hydrogen, $C_1$–$C_6$ straight chain alkyl, $C_3$–$C_6$ branched chain alkyl, $C_3$–$C_7$ cycloalkyl, phenyl, or —$CH_2$-phenyl;

$R_{12}$ and $R_{12'}$ are independently selected from the group of hydrogen, $C_1$–$C_6$ straight chain alkyl, $C_3$–$C_6$ branched chain alkyl, $C_3$–$C_7$ cycloalkyl, phenyl, substituted phenyl, —$CH_2$-phenyl or —$CH_2$-substituted phenyl, the $C_3$–$C_7$ cycloalkyl groups being optionally substituted by from 1 to 3 groups independently selected from $R_5$ to $R_9$;

with a proviso that both $R_{12}$ and $R_{12'}$ in the moiety:

are not phenyl or substituted phenyl;

$R_{12}$ and $R_{12'}$ may also optionally be taken together with their associated carbon to form a carbocyclic ring of from three to seven carbon atoms;

$R_{13}$ is an amino-protecting group used to protect the moiety $NR_{11}$ herein which may be any group known to be useful to protect amino groups under the conditions contemplated as outlined in Greene, *Protective Groups in Organic Synthesis* Volume 2, Chapter 7, 1991, and references therein. Examples of such useful amino protecting groups include but are not limited to:

(a) acyl type protective groups such as formyl, acetyl, chloroacetyl, dichloroacetyl, trichloroacetyl, trifluoroacetyl, phenylacetyl, o-nitrophenoxyacetyl, sec-butyryl, pivaloyl- (also known as tert-butyryl), cyclopropanoyl, benzoyl, o-nitrobenzoyl, α-chlorobutyryl, or the like; or (b) sulfonyl type protecting groups such as benzenesulfonyl, toluenesulfonyl (tosyl), p-methoxybenzenesulfonyl, trifluoromethylsulfonyl, or the like; or (c) sulfonyl type protecting groups such as benznesulfenyl, o-nitrobenzenesulfenyl, pentachlorobenzenesulfenyl, and the like; or (d) urethane type protecting groups such as benzyloxycarbonyl, p-chlorobenzyloxycarbonyl, p-nitrobenzyloxycarbonyl, p-bromobenzyloxycarbonyl, p-methoxybenzyloxycarbonyl, o-nitrobenzyloxycarbonyl, tert-butyloxycarbonyl, tert-amyloxycarbonyl, diisopropylmethoxycarbonyl, isopropyloxycarbonyl, allyloxycarbonyl, cyclopentyloxycarbonyl, adamantyloxycarbonyl, cyclohexyloxycarbonyl, 9-fluorenylmethoxycarbonyl, 2-trimethylsilylethoxycarbonyl, and the like.

The moiety $NR_{11}R_{13}$ may also be optionally concatenated together or exist as a cyclic imide of the formula:

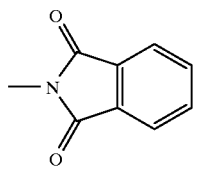

the process comprising converting an amine N-oxide of the formula (II):

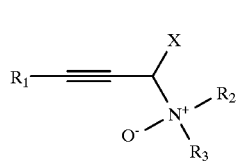

(II)

to the enaminone by treating the amine N-oxide with a hydroxylic solvent.

It is understood herein that the definitions of the compounds of formula (I), above and below, when X, $R_1$, $R_2$, $R_3$, $R_4$, $R_{4'}$, $R_5$, $R_6$, $R_7$, $R_8$, $R_9$, $R_{10}$, $R_{11}$, $R_{11'}$, $R_{12}$, $R_{12'}$ or $R_{13}$ contain asymmetric carbons, encompass all possible stereoisomers and mixtures thereof discussed below. In particular, it encompass any optical isomers and diastereomers; as well as the racemic and resolved, enantiomerically pure R and S stereoisomers; as well as other mixtures of the R and S stereoisomers and pharmaceutically acceptable salts thereof. Optical isomers may be obtained in pure form by standard separation techniques.

It is also understood herein that the definitions of X, $R_1$, $R_2$, $R_3$, $R_4$, $R_{4'}$, $R_5$, $R_6$, $R_7$, $R_8$, $R_9$, $R_{10}$, $R_{11}$, $R_{11'}$, $R_{12}$, $R_{12'}$ or $R_{13}$ of the compounds of formula (I), a and below, encompasses all possible regioisomers, and mixtures thereof discussed below. Such regioisomers may be obtained pure by standard separation methods known to those skilled in the art.

Among the subgroups of the groups disclosed herein are those in which $R_{12}$ and $R_{12'}$ are selected from non-substituted phenyl or benzyl. Another subgroup among those disclosed herein are those in which the —$CH_2$-phenyl groups symbolized by X are unsubstituted.

A preferred process within the scope of this invention provides for the synthesis of enaminones of Formula (I):

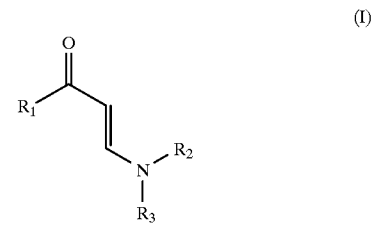

(I)

wherein $R_1$ is selected from the group of $C_1$–$C_6$ straight chain alkyl, $C_3$–$C_6$ branched chain alkyl, $C_3$–$C_7$ cycloalkyl, phenyl, —$CH_2$-phenyl, or the moieties:

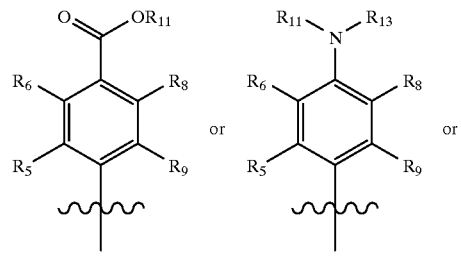

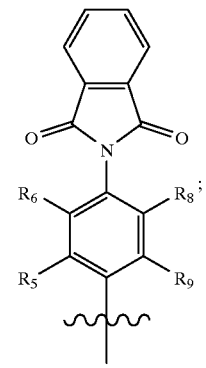

$R_2$ and $R_3$ are independently selected from the group of $C_1$–$C_6$ straight chain alkyl, $C_3$–$C_6$ branched chain alkyl, $C_3$–$C_7$ cycloalkyl, or —$CH_2$-phenyl. $R_2$ and $R_3$ may also be joined to form a ring of from three to six atoms to create cyclic versions of —$NR_2R_3$, which include, but are not limited to, the following:

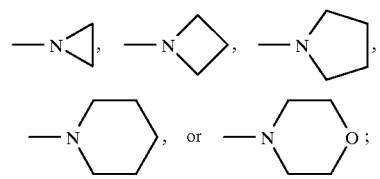

$R_5$, $R_6$ $R_8$, $R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)OR_{11'}$, —$NR_{11}C(O)R_{11'}$, —$OC(O)R_{11}$, —$OC(O)OR_{11}$, or —$OC(O)NHR_{11}$;

$R_{11}$ and $R_{11'}$ are selected from the group of hydrogen, $C_1$–$C_6$ straight chain alkyl, $C_3$–$C_6$ branched chain alkyl, $C_3$–$C_7$ cycloalkyl, phenyl, or —$CH_2$-phenyl;

$R_{13}$ is selected from the group of hydrogen, $C_1$–$C_6$ straight chain alkyl, $C_3$–$C_6$ branched chain alkyl, $C_3$–$C_7$ cycloalkyl, phenyl, or an amino-protecting group used to transiently protect the moiety $NR_{11}$ herein which may be any group known to be useful to protect amino groups under the conditions contemplated as outlined in Greene, *Protective Groups in Organic Synthesis* Volume 2, Chapter 7, 1991, and references therein. Examples of such useful amino protecting groups include, but are not limited to, those described above;

the process comprising converting an amine N-oxide of the formula (II):

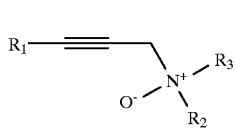

(II)

to the enaminone by treating the amine N-oxide with a hydroxylic solvent.

Another preferred process within the scope of this invention provides for the synthesis of enarinones of Formula (I):

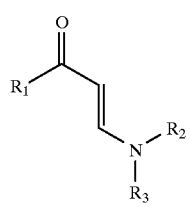

(I)

wherein $R_1$ is the moiety:

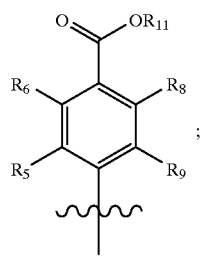

$R_2$ and $R_3$ are independently is selected from the group of $C_1$–$C_6$ straight chain alkyl, $C_3$–$C_6$ branched chain alkyl, —$CH_2$-phenyl or $C_3$–$C_7$ cycloalkyl. $R_2$ and $R_3$ may also be joined to form a ring of from three to six atoms. Thus, for example, cyclic versions of —$NR_2R_3$ include but are not limited to the following:

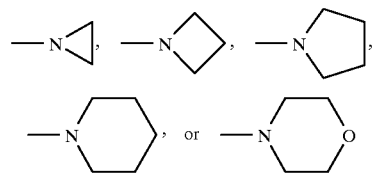

$R_5$, $R_6$ $R_8$, $R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)OR_{11'}$, —$NR_{11}C(O)R_{11'}$, —$OC(O)R_{11}$, —$OC(O)OR11$, or —$OC(O)NHR_{11}$;

$R_{11}$ and $R_{11'}$ are selected from the group of hydrogen, $C_1$–$C_6$ straight chain alkyl, $C_3$–$C_6$ branched chain alkyl, $C_3$–$C_7$ cycloalkyl, phenyl, or —$CH_2$-phenyl;

$R_{13}$ is selected from the group of hydrogen, $C_1$–$C_6$ straight chain alkyl, $C_3$–$C_6$ branched chain alkyl, $C_3$–$C_7$ cycloalkyl, phenyl, or an amino-protecting group used to transiently protect the moiety $NR_{11}$ herein which may be any group known to be useful to protect amino groups under the conditions contemplated as outlined in Greene, *Protective Groups in Organic Synthesis* Volume 2, Chapter 7, 1991, and references therein. Examples of such useful amino protecting groups include those described above.

The moiety $NR_{11}R_{13}$ may also optionally exist as a cyclic imide of the formula:

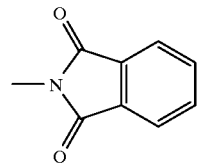

the process comprising converting an amine N-oxide of the formula (II):

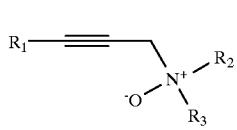

(II)

to the enaminone by treating the amine N-oxide with a hydroxylic solvent.

A further preferred process within the scope of this invention provides for the synthesis of enaminones of Formula (I):

(I)

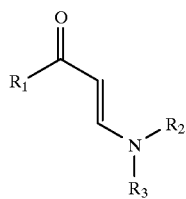

wherein $R_1$ is the moiety:

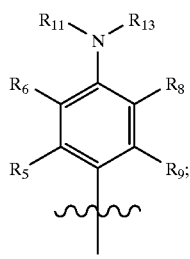

$R_2$ and $R_3$ are independently selected from the group of $C_1$–$C_6$ straight chain alkyl, $C_3$–$C_6$ branched chain alkyl, —$CH_2$-phenyl or $C_3$–$C_7$ cycloalkyl. $R_2$ and $R_3$ may also be joined to form a ring of from three to six atoms. Thus, for example, cyclic versions of —$NR_2R_3$ include but are not limited to the following:

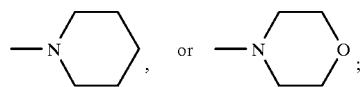

$R_5$, $R_6$, $R_8$, $R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)OR_{11'}$, —$NR_{11}C(O)R_{11'}$, —$OC(O)R_{11}$, —$OC(O)OR_{11}$, or —$OC(O)NHR_{11}$;

$R_{11}$ and $R_{11}'$ are independently selected from the group of hydrogen, $C_1$–$C_6$ straight chain alkyl, $C_3$–$C_6$ branched chain alkyl, $C_3$–$C_7$ cycloalkyl, phenyl, or —$CH_2$-phenyl;

$R_{13}$ is selected from the group of hydrogen, $C_1$–$C_6$ straight chain alkyl, $C_3$–$C_6$ branched chain alkyl, $C_3$–$C_7$ cycloalkyl, phenyl, or an amino-protecting group used to transiently protect the moiety $NR_{11}$ herein which may be any group known to be useful to protect amino groups under the conditions contemplated as outlined in Greene, *Protective Groups in Organic Synthesis* volume 2, Chapter 7, 1991, and references therein. Examples of such useful amino protecting groups include, but are not limited to, those described above.

The moiety $NR_{11}R_{13}$ may also optionally exist as a cyclic imide of the formula:

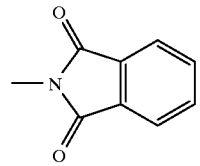

the process comprising converting an amine N-oxide of the formula (II):

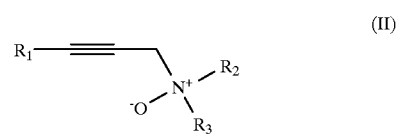

to the enaminone by treating the amine N-oxide with a hydroxylic solvent.

Another preferred process of this invention provides for synthesis of enaminones of the formula:

(I)

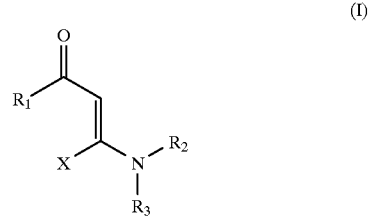

wherein:

X is selected from the group of H, $C_1$–$C_6$ straight chain alkyl, $C_3$–$C_6$ branched chain alkyl, $C_3$–$C_7$ cycloalkyl, phenyl, or —$CH_2$-phenyl;

$R_1$ is selected from the group of hydrogen, $C_1$–$C_6$ straight chain alkyl, $C_3$–$C_6$ branched chain alkyl, $C_3$–$C_7$ cycloalkyl, phenyl, substituted phenyl, —$CH_2$-phenyl, or —$CH_2$-substituted phenyl, the substituents of which are as described above, or a group of the formulae:

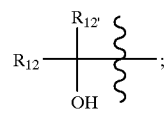

$R_2$ and $R_3$ are independently is selected from the group of $C_1$–$C_6$ straight chain alkyl, $C_3$–$C_6$ branched chain alkyl, or $C_3$–$C_7$ cycloalkyl. $R_2$ and $R_3$ may also be joined to form a ring of from three to six atoms. Thus, for example, cyclic versions of —$NR_2R_3$ include, but are not limited to, the following:

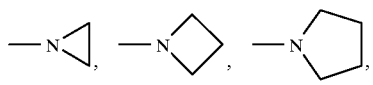

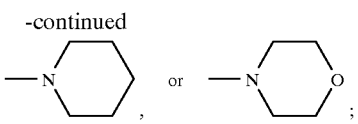

$R_{12}$ and $R_{12'}$ are independently selected from the group of hydrogen, $C_1$–$C_6$ straight chain alkyl, $C_3$–$C_6$ branched chain alkyl, $C_3$–$C_7$ cycloalkyl, phenyl, or —CH$_2$-phenyl, the $C_3$–$C_7$ cycloalkyl, phenyl, and —CH$_2$-phenyl being optionally substituted as described in the groups above;

with a proviso that $R_{12}$ and R12' are not both phenyl or substituted phenyl;

the process comprising converting an amine N-oxide of the formula (II):

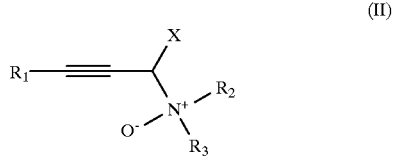

(II)

to the enaminone (I) by treating the amine N-oxide (II) with a hydroxylic solvent.

The conversion of the amine N-oxide into an enaminone may be accomplished by a number of embodiments within the scope of this invention. The amine N-oxide may be introduced into a suitable hydroxylic solvent, preferably with stirring, at or between about room or ambient temperature and about the reflux temperature of the solvent. In other instances the introduction of the amine N-oxide to a hydroxylic solvent, preferably with stirring, may be accomplished in the presence of an acceptable catalyst, such as a palladium(II) catalyst or a copper (I) catalyst, at or between room temperature and the reflux temperature of the solvent.

In instances where a biphasic solvent system is desirable, the amine N-oxide may be converted into the enaminone in a biphasic mixture of water and a water immiscible solvent, such as dichloromethane, in the presence or absence of a suitable catalyst, such as a palladium(II) catalyst or a copper (I) catalyst, and a phase transfer catalyst, such as a quaternary ammonium salt, at or between ambient temperature and the reflux temperature of the organic solvent, preferably with stirring.

The amine N-oxides converted in this process may be formed by oxidizing an amine of the formula (III):

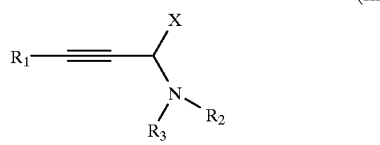

(III)

wherein X, $R_1$, $R_2$, and $R_3$ are defined above, using any of a number of standard oxidative procedures (Albini, A. *Synthesis* 1993, 263) or with dioxirane reagents (Murray, R. W. *Chem. Rev.* 1989, 1187).

In another embodiment, this invention comprises a process for converting an amine of Formula (III) to an enaminone of Formula (I), the process comprising the steps of:

a) oxidizing the amine of Formula (III) to an amine N-oxide of Formula (II), which may be accomplished by conventional techniques; and b) converting the amine N-oxide of step a) to an enaminone of Formula (I) by treating the amine N-oxide with a hydroxylic solvent in a manner described above.

The hydroxylic solvents useful with this invention may be defined as any solvent or combination of solvents composed of or containing water, any $C_1$–$C_8$ straight chain or branched chain alkyl alcohol, ethylene glycol, polyethylene glycol, 1,2-propylene diol, polypropylene glycol, glycerol, 2-methoxyethanol, 2-ethoxyethanol, 2,2,2-trifluoroethanol, benzyl alcohol, phenol, or any equivalent solvent that contains one or more free hydroxyl (—OH) substituent(s) that is known to those skilled in the art.

Solvent systems containing one or more cosolvents, along with one or more solvents may be used for the processes of this invention. The cosolvents referred to herein may be defined as a diluent of the main solvent(s) and can be selected from: hydrocarbons such as pentane, hexane or heptane; aromatic hydrocarbon such as benzene, toluene or xylene; ethers such as diethyl ether, tetrahydrofum, dioxane or dimethoxy ethane; chlorinated hydrocarbons such as dichloromethane, chloroform, dichloroethane, or tetrachloroethane; or other common solvents such as ethyl acetate, N,N-dimethylformamide, N,N-dimethylacetamide, acetonitrile, dimethylsulfoxide, acetone, or the like.

The compounds of formula (III) above wherein $R_1$ is defined as:

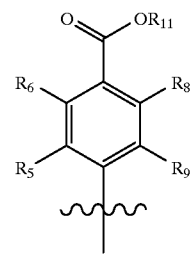

wherein $R_2$, $R_3$, $R_5$, R6, $R_8$, $R_9$, and $R_{11}$ are as defined above, may be readily prepared from the corresponding aryl bromide, iodide, or triflate in a manner similar to that described in the literature (e.g. Sanogashira, et.al. *Tetrahedron Lett.* 1975, 4467; Unroe, et.al. *Synthesis-Stuttgart* 1987, 981) and are readily converted by any of a number of standard oxidative methods (Albini, A. *Synthesis* 1993, 263) or by treatment with dioxirane reagents (Murray, R. W. *Chem. Rev.* 1989, 1187) to their respective N-oxides, which can then be converted by the processes described above to compounds of structural formula I. Such compounds are useful for the preparation of substances with vasopressin agonist activity as exemplified by compounds 10 and 11 as shown in Scheme I.

Scheme I
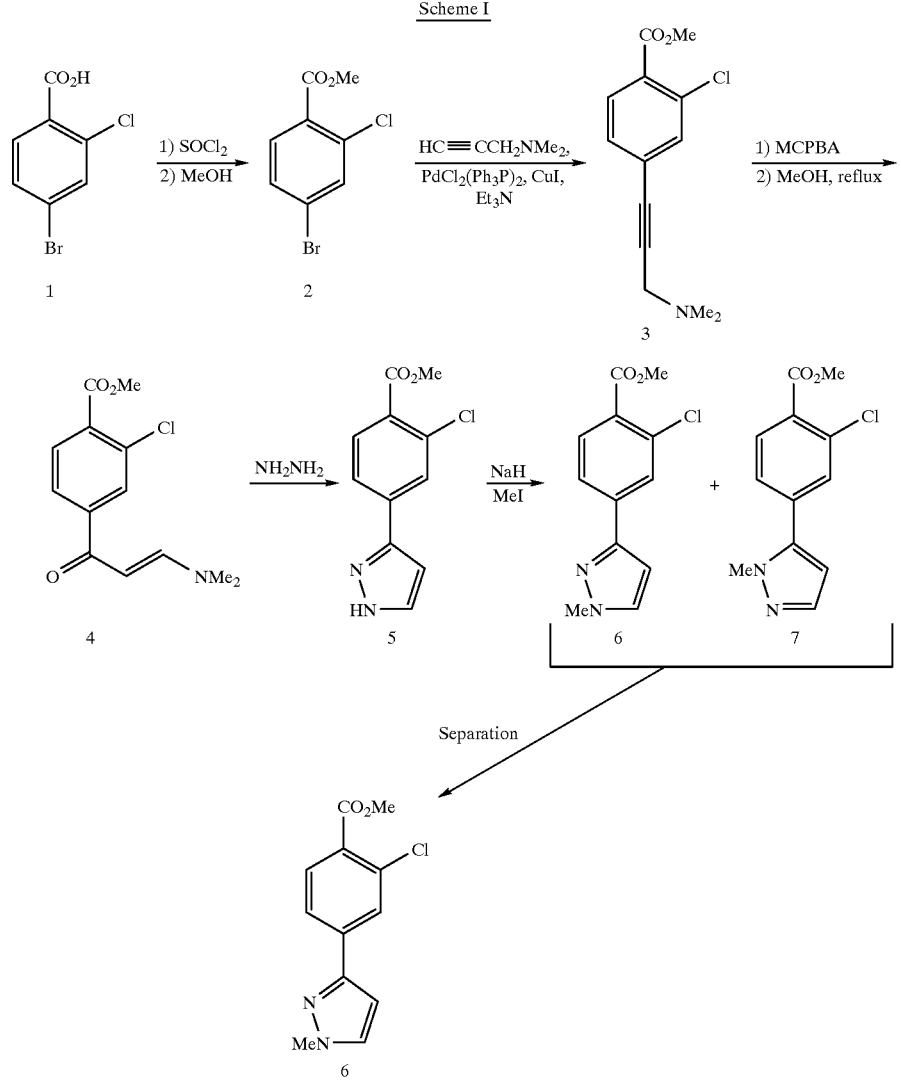

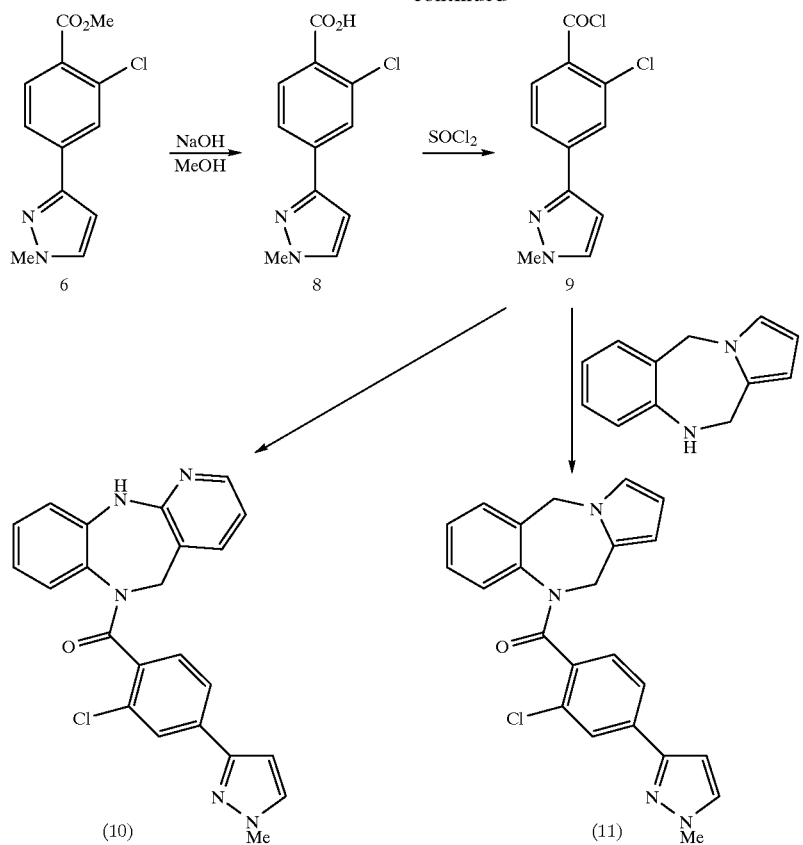

Thus, the bromocarboxylic acid 1, is converted into the corresponding ester 2 by treating the carboxylic acid with thionyl chloride at temperatures ranging from ambient to the reflux temperature of the solvent, or with oxalyl chloride in an aprotic solvent such as dichloromethane or tetrahydrofuran in the presence of a catalytic amount of dimethylformamide at temperatures ranging from 0° C. to 40° C. followed by the addition of methanol. The methylester of formula 2 is coupled with a dialkylamino propyne, preferably 1-dimethylarino propyne, in the presence of a catalyst such as bis(triphenylphosphine) palladium(II) chloride and copper(I) iodide in an organic base such as triethylamine as the solvent and at temperatures ranging from ambient to 80° C. essentially according to the procedures of Alami et al. *Tetrahedron Lett* 1993, 34, 6403, and of Sanogashira et al. *Tetrahedron Lett.* 1975, 4467 to provide the substituted acetylene 3. The intermediate 3 is subsequently converted into its N-oxide by treatment with an oxidizing agent using any of a number of standard oxidative procedures (Albini, A. *Synthesis* 1993, 263) or with dioxirane reagents (Murray, R. W. *Chem. Rev.* 1989, 1187), in an aprotic organic solvent such as dichloromethane at temperatures below ambient. The intermediate N-oxide is not isolated but is rearranged in situ to an enone of formula 4 by heating in a hydroxylic solvent such as methanol or by using any of the procedures described herein.

Treatment of 4 with hydrazine in acetic acid at temperatures ranging from ambient to reflux temperature of the solvent leads to a compound of formula 5. The heterocyclic nitrogen in compound 5 is alkylated by treatment with a strong base such as sodium or potassium hydride and methyl iodide in an aprotic organic solvent such as dimethylformarnide or tetrahydrofuran at temperatures ranging from 0° C. to 80° C. leading to a mixture of regioisomers 6 and 7. The major isomer, compound 6, is separated by means of chromatography and/or crystallization and subsequently hydrolyzed with an aqueous base such as sodium hydroxide in methanol (or lithium hydroxide in tetrahydrofuran) to the desired carboxylic acid of formula 8.

The intermediate carboxylic acid 8 is then converted into an acylating species, preferably an acid chloride (bromide or iodide) of formula 9 by procedures analogous to those described hereinbefore. The acylating agent 9 is then used to acylate a tricyclic benzodiazepine such as either 10,11-dihydro-5H-pyrrolo[2,1-c][1,4]benzodiazepine (Albright etal. U.S. Pat. No. 5,536,718 Jul. 16, 1996) or 6,11-dihydro-5H-pyrido{2,3-b][1,5]benzodiazepine to afford compounds 10 and 11, respectively.

The compounds of formula III wherein $R_1$ is defined as:

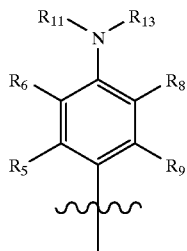

wherein $R_2$, $R_3$, $R_5$, $R_6$, $R_8$, $R_9$, $R_{11}$ and $R_{11'}$ are as defined above, may be readily prepared from the corresponding aryl bromide, iodide, or triflate in a manner similar to that described in the literature (e.g. Sanogashira, et.al. *Tetrahedron Lett* 1975, 4467; Unroe, et.al. *Synthesis-Stuttgart* 1987, 981) and are readily converted by any of a number of standard oxidative methods (Albini, A. *Synthesis* 1993, 263) or by treatment with dioxirane reagents (Murray, R. W. *Chem. Rev.* 1989, 1187) to their respective N-oxides, which can then be converted by the processes described above to compounds of structural formula I. Such compounds are useful for the preparation of substances with vasopressin agonist activity as exemplified by compounds 10 and 11 as shown in Schemes I and II.

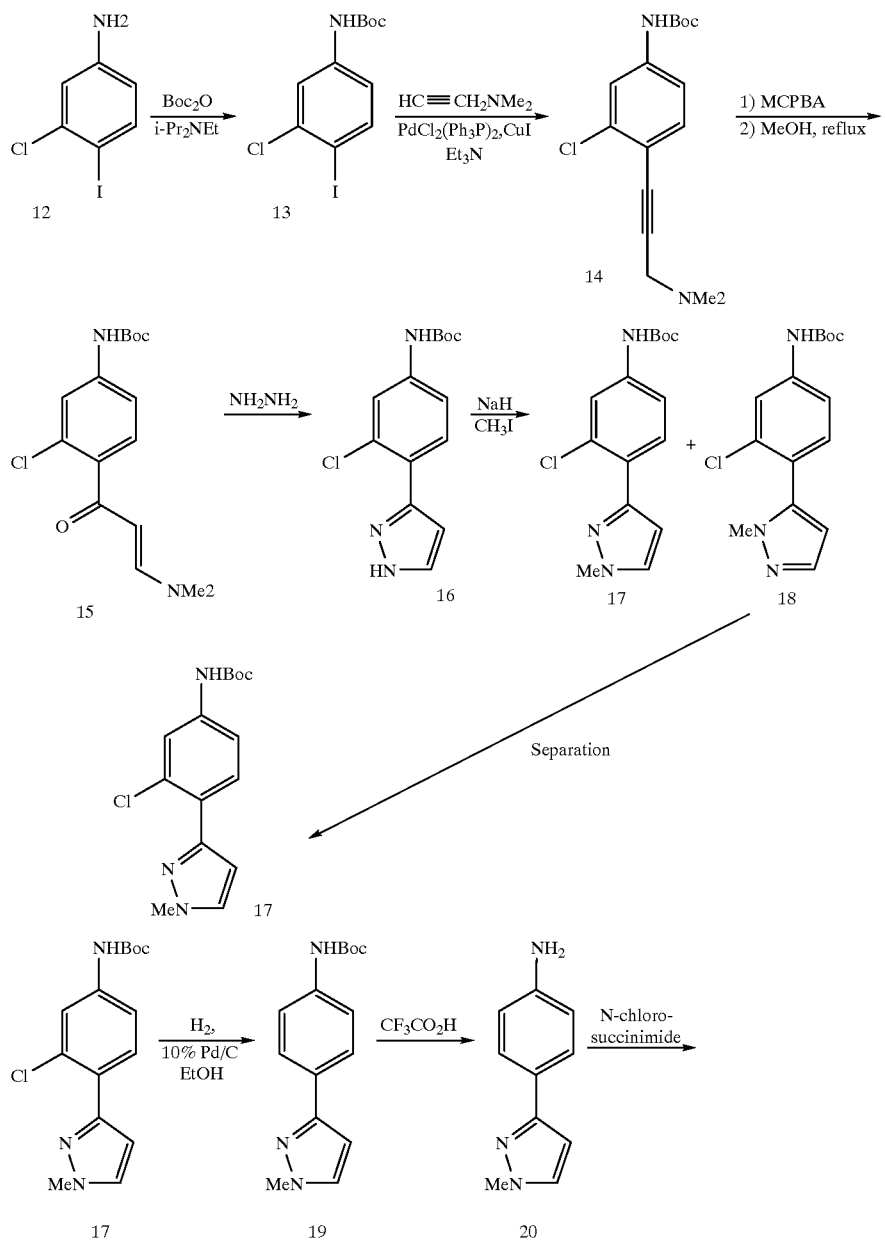

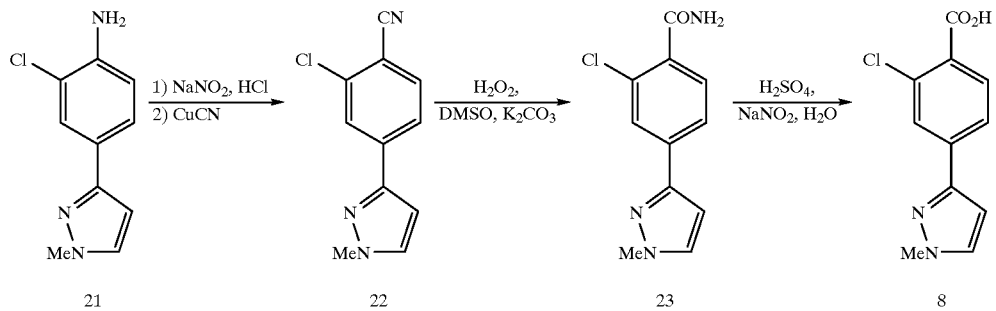

The enaminone 15 (and thence compounds 10 and 11) may also be prepared utilizing this novel chemistry starting from 3-chloro4-iodo aniline (12) through the sequence of steps shown in Scheme II. The aniline derivative 12 is treated with di-tert-butyl dicarbonate and diisopropylethylamine in refluxing tetrahydrofuran to afford compound 13. The aryliodide derivative of formula 13 is coupled with a dialkylamino propyne, preferably 1-dimethylamino propyne, in the presence of a catalyst such as bis (triphenylphosphine) palladium(II) chloride and copper(I) iodide in an organic base such as triethylamine as the solvent and at temperatures ranging from ambient to 80° C. essentially according to the procedures of Alami et al., *Tetrahedron Lett.*, 34, 6403 (1993), and of Sanogashira et al., *Tetrahedron Lett*, 4467 (1975) to provide the substituted acetylene 14. The intermediate 14 is subsequently converted into its N-oxide by treatment with an oxidizing agent using any of a number of standard oxidative procedures (Albini, A. *Synthesis* 263 (1993) or with dioxirane reagents (Murray, R. W., *Chem. Rev.* 1187 (1989), in an aprotic organic solvent such as dichloromethane at temperatures below ambient. The intermediate N-oxide is not isolated but is rearranged in situ to an enaminone of formula 15 by heating in a hydroxylic solvent such as methanol or by using any of the procedures described herein.

Treatment of 15 with hydrazine in acetic acid at temperatures ranging from ambient to reflux temperature of the solvent leads to a compound of formula 16. The heterocyclic nitrogen in compound 16 is alkylated by treatment with a strong base such as sodium or potassium hydride and methyl iodide in an aprotic organic solvent such as dimethylformamide or tetrahydrofuran at temperatures ranging from 0° C. to 80° C. leading to a mixture of regioisomers 17 and 18. The major isomer, compound 17, may be separated by means of chromatography and crystallization.

The substituted pyrazole derivative 17 may be dehalogenated by hydrogenation over palladium catalysts in alcohol solvents (Weizmann, A. *J. Am. Chem. Soc.* 1949, 71, 4154), to afford 19 and then Boc-deprotected by treatment with trifluoroacetic acid to give the pyrazoloaniline 20. This aniline derivative 20 may be chlorinated by treatment with N-chlorosuccinimide (Neale, R. S. et.al. *J. Org. Chem.* 1964, 29, 3390) to yield compound 21 which is then subjected to the Sandmeyer reaction (Clarke, H. T. et.al. *Organic Synthesis*, Vol. I, 1941, 514) to provide nitrite 22.

Compound 22 may be converted to the carboxylic acid 8 by sequential treatment with basic hydroperoxide (Katritzky, A. R. et.al. *Synthesis* 1989, 949) followed by hydrolysis of the resulting amide 23 by treatment with dilute sulfuric acid and sodium nitrite (Hales, N. J. et al., *Tetrahedron* 1995, 51, 7403). The conversion of carboxylic acid 8 to the vasopressin agonists 10 and 11 is shown in Scheme I above.

Structures 10 and 11 are non-peptide mimics of vasopressin (antidiuretic hormone, ADH), a nine amino acid peptide hormone and neurotransmitter. Vasopressin plays a vital role in the body's conservation of water by concentrating the urine at the site of the collecting ducts of the kidney. The collecting ducts of the kidney are relatively impermeable to water in the absence of vasopressin at its receptors and therefore, the hypotonic fluid formed after filtering through the glomeruli, passing the proximal convoluted tubules, the loops of Henle, and the distal convoluted tubules, will be excreted as dilute urine. However, during dehydration, volume depletion or blood loss, vasopressin is released from the pituitary and activates the vasopressin $V_2$ receptors in the collecting ducts of the kidney rendering the ducts very permeable to water, and hence water is reabsorbed and a concentrated urine is excreted. In patients and animals with central or neurogenic diabetes insipidus, the synthesis of vasopressin in the pituitary is defective and therefore, they produce no or very little vasopressin, but their vasopressin receptors in the kidneys are normal. While they remain very sensitive to the action of vasopressin and vasopressin V2 agonists, little or no vasopressin is produced. Because they cannot concentrate the urine, they may produce as high as 10 times the urine volume of their healthy counterparts. Vasopressin and desmopressin, which is a peptide analog of the natural vasopressin, are being used in patients with central diabetes insipidus. Vasopressin V2 agonists are also useful for the treatment of nocturnal enuresis, nocturia, urinary incontinence and temporary delay of urination whenever desirable.

The vasopressin-like compounds, prepared using the intermediates disclosed in this invention, posses therapeutic effects similar to vasopressin without the limitations associated with peptide derived drugs.

Compounds 10 (Example 22) and 11 (Example 23) of the present invention were tested for biological activity according to the following procedure:

Vasopressin $V_2$ Agonist Effects of Test Compounds in Normal Conscious Water-Loaded Rats:

Male or female normotensive Sprague-Dawley rats (Charles River Laboratories, Inc., Kingston, N.Y.) of 350–500 g body weight were supplied with standard rodent diet (Purina Rodent Lab. Chow 5001) and water ad libitum. On the day of test, rats were laced individually into metabolic cages equipped with devices to separate the feces from the urine and containers for collection of urine. Test compound or reference agent was given at an oral dose of 10 mg/kg in a volume of 10 ml/kg. The vehicle used was 20% dimethylsulfoxide (DMSO) in 2.5% preboiled corn starch. Thirty minutes after dosing the test compound, rats were gavaged with water at 30 ml/kg into the stomach using a feeding needle. During the test, rats were not provided with water or food. Urine was collected for four hours after dosing of the test compound. At the end of four hours, urine volume was measured. Urinary osmolality was determined using a Fiske One-Ten Osmometer (Fiske Associates, Norwood, Mass., 02062) or an Advanced CRYOMATIC Osmometer, Model 3C2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used.

| Compound # | Example # | Urine Volume (% decrease)[a] | Osmolality Increase[b] | Rat Type[c] |
|---|---|---|---|---|
| 10 | 22 | 70% | 325% | CD |
| 11 | 23 | 80% | 272% | CD |

[a] Percent decrease in urine volume vs. control at a dose of 10 mg per kg.
[b] Osmolality increase expressed as percent of control at a dose of 10 mg per kg.
[c] Rat model used: Sprague-Dawley (CD).

The compounds wherein $R_1$ above in formula (III) is defined as:

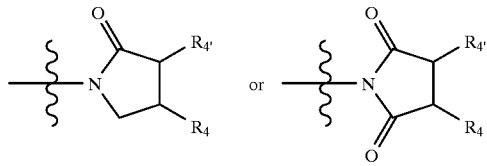

wherein $R_4$ is hydrogen and $R_2$ and $R_3$ are defined as above, may be readily prepared from procedures outlined by Dickinson et al. U.S. Pat. No. 3,354,178;

wherein $R_4$ is hydrogen and $R_2$ and $R_3$ are also joined to form a pyrrolidine ring is readily obtained commercially as oxotremorine and, wherein $R_4$ is defined as above but not hydrogen and $R_2$ and $R_3$ are defined as above, may be readily prepared from procedures outlined by Trybulski et al. U.S. Pat. Nos. 5,550,257 and 4,937,235;

Reduction of compound 24 wherein $R_2$, $R_3$ and $R_4$ are defined as above

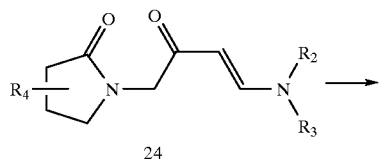

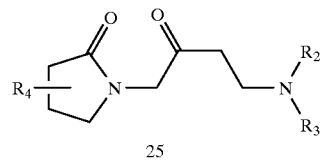

with hydrogen in the presence of a transition metal catalyst such as palladium on carbon, platinum oxide or raney nickel in an alcohol solvent such as ethanol, or alternatively by Lewis acid assisted reduction by certain metal hydride reagents, such as by the exposure to boron trifloride etherate and lithium triethylborohydride in tetrahydrofuran at reduced temperatures (as per the methods of Wasserman and Chi, *Tetrahedron Letters* 1994, 35 (52), 9779), or by exposure to boron trifloride etherate and a copper hydride species generated from cuprous bromide dimethyl sulfide complex and lithium dimethoxyaluminium hydride (as per the methods of Commmmns and LaMunyon, *Tetrahedron Letters* 1989, 30 (38), 5053) produce compound 25. Compounds of structure 25 are hydrolytic and possibly metabolic products of oxotremorine-like compounds (Lindeke, B. J. Pharrnn. Pharmac., 1972, 24, 25–31).

The compounds of formula (III) above wherein $R_1$ is defined as:

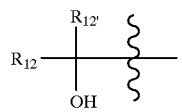

wherein $R_{12}$ and $R_{12'}$ are defined above, may be readily prepared by addition of the lithium anion of a propargylic ammnnine by methods known to those skilled in the art, or alternatively and when X as defined above is not H, by addition of the bis-lithium anion of a propargylic alcohol to a 1-(dialkylaminomethyl)benzotriazole (Katritzky, A. R.; Gallos, J. K.; Yannakopoulou, K. *Synthesis* 1989, 31), and are readily converted by any of a number of standard oxidative methods (Albini, A. *Synthesis* 1993, 263) or by treatment with dioxirane reagents (Murray, R. W. *Chem. Rev.* 1989, 1187) to their respective N-oxides, which can then be converted by the processes described above to compounds of structural formula I. Such compounds are useful for the preparation of certain 3(2H)-furanone intermediates (by exposure to acidic conditions as demonstrated by Carpenter, B. K.; Clemens, K. E.; Schmidt, E. A.; Hoffmann, H. M. R. *J. Am. Chem. Soc.* 1972, 94(17), 6213) which can be converted into compounds which possess anticholesteremic and antidiabetic properties as described in Felman, et.al. U.S. Pat. No. 5,314,913, May 24, 1994 as shown in Scheme III.

Scheme III

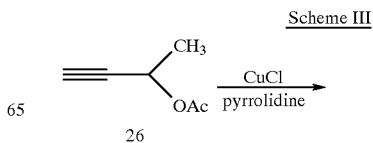

-continued

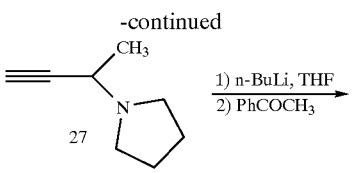

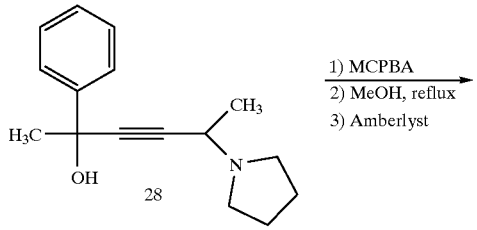

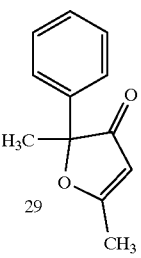

Thus, the propagylic amine 27 may be prepared by the copper-catalyzed displacement of the propargylic acetate 26 (which is readily prepared according to the methods of Clarke and Pinder, *J. Chem. Soc.* 1958, 1967) by pyrrolidine. The propargylic amine 27 may be mono-lithiated at the terminal position by treatment at temperatures below ambient, preferably about −78° C., in tetrahydrofuran with a slight molar excess of n-butyl lithium and then added to acetophenone to provide the 20 propargylic amino alcohol 28. Intermediate 28 is subsequently converted into its N-oxide by treatment with an oxidizing agent using any of a number of standard oxidative procedures (Albini, A. *Synthesis* 1993, 263) or with dioxirane reagents (Murray, R. W. *Chem. Rev.* 1989, 1187), in an aprotic organic solvent such as dichloromethane at temperatures below ambient. The intermediate N-oxide is not isolated but is rearranged in situ to an enone (which also need not be isolated) by heating in a hydroxylic solvent such as methanol or by using any of the procedures described herein. This enone is then treated in situ with an acid catalyst such as Amberlyst® which completes the cyclization with loss of pyrrolidine to produce the substituted 3(2H)-furanone that has previously been converted into numerous substances with anticholesteremic and antidiabetic properties as described by Felman et.al. in U.S. Pat. No. 5,314,913, issued May 24, 1994.

The process of the present invention will be further illustrated by the following non-limiting examples.

EXAMPLE 1

1-Dimethylamino-4-[1-(3-(R)-O-octylcarbamoyl-2-oxo-pyrrolidinyl]-2-butyne N-oxide To an ice cold solution of (R)-octylcarbarnic acid-1-(4-(dimethylammino)-2-butynyl)-2-oxo-3-pyrrolidinyl ester (250 mg) in dichloromethane (6 ml) was added dropwise a solution of dimethyldioxirane in acetone (approximately 0.08 M, 9 ml). After the reaction was stirred at 0° C. for 20 minutes, the solvent was removed under a gentle stream of argon. Trituration of the residue with diethyl ether gave the desired N-oxide as a white powder. MS(+ES), m/z: 368 (M+H)⁺.

EXAMPLE 2

1-Dimethylamino-4-[1-(3-(R)-hydroxy-2-oxo-pyrrolidinyl]-2-butyne N-oxide

To an ice cold solution of (R)-1-(4-(dimethylamino)-2-butynyl)-3-hydroxy-2-pyrrolidinone (250 mg) in dichloromethane (8 ml) was added dropwise a solution of dimethyldioxirane in acetone (approximately 0.08 M, 17.8 ml). After the reaction was stirred at 0° C. for 20 minutes, the solvent was removed under a gentle stream of argon to give the desired N-oxide as a yellow foam. MS(+ES), m/z: 213 (M+H)⁺.

EXAMPLE 3

(R)-Octylcarbamic acid-1-[4-(dimethylamino)-2-oxo-3-butenyl]-2-oxo-3-pyrrolidinyl ester A solution of 1-dimethylamino-4-(1-(3-(R)-O-octylcarbamoyl-2-oxo-pyrrolidinyl)-2-butyne N-oxide (25 mg) in methanol (1.5 ml) was heated to 60° C. for 5 hours. The mixture was cooled and the solvent evaporated to dryness in vacuo. The residue was chromatographed over silica gel (5% methanol in dichloromethane was used as the eluant) to give upon evaporation of the solvent in vacuo the title compound as a colorless oil. MS(FAB), m/z: 368 (M+H)⁺.

EXAMPLE 4

(R)-1-[4-(Dimethylamino)-2-oxo-3-butenyl]-3-hydroxy-2-pyrrolidinone

A solution of 1-dimethylamino-4-[1-(3-(R)-hydroxy-2-oxo-pyrrolidinyl]-2-butyne N-oxide (250 mg) in methanol (10 ml) was heated to 60° C. for 6 hours. The mixture was cooled and the solvent evaporated to dryness in vacuo. The residue was chromatographed over silica gel (5–20% methanol in dichloromethane was used as the eluant) to give upon evaporation of the solvent in vacuo the title compound. MS(FAB), m/z: 213 (M+H)⁺.

EXAMPLE 5

1-[4-(1-Pyrrolidino)-2-oxo-3-butenyl]-2-pyrrolidinone

To an ice cold solution of oxotremorine (412 mg) in dichloromethane (4 ml) was added in small portions 3-chloroperoxybenzoic acid (362 mg). After the reaction was stirred at 0° C. for 20 minutes, the mixture was passed over twenty weight equivalents of basic alumina (Brockmann Grade I, 150 mesh) and the N-oxide was eluted using a solution of 5% methanol in dichloro-methane. All fractions containing the desired amine N-oxide were combined and evaporated to near dryness in vacuo. The residue was treated successively three times with small portions of methanol (ca. 25 ml) followed by evaporation to near dryness, and the volume of the solution was adjusted to 30 mL by addition of methanol. The methanolic solution of the N-oxide was heated to reflux for approximately 5 hours, cooled, and the solvent was evaporated to dryness in vacuo. . The residue was chromatographed over silica gel (4% methanol in dichloromethane was used as the eluant) to give upon evaporation of the solvent in vacuo an crystallization from ethyl acetate-hexanes the title compound as colorless prisms. m.p. 99–101° C. MS(+ES), m/z: 223 (M+H)$^+$.

EXAMPLE 6

1-Dimethylamino-3-phenyl-2-propyne N-oxide

To an ice cold solution of 1-dimethylamino-3-phenyl-2-propyne (1.0 g; prepared by the Mannich reaction of phenylacetylene with formaldehyde and dimethylamine; Mannich *Chem. Ber.* 1933, 66, 418; Lattes, et.al. *Tetrahedron* 1982, 38, 2355) in dichloromethane (15 ml) was added in small portions 3-chlorophenylperoxybenzoic acid (1.13 g) over a period of about 2 minutes. After the reaction was stirred at 0° C. for 20 minutes, the mixture was passed over twenty weight equivalents of basic alumina (Brockmann Grade I, 150 mesh) and eluted with 5% methanol in dichloromethane. All fractions containing the desired amine N-oxide were combined and evaporated to near dryness in vacuo. Ether was added to precipitate the product as a colorless solid. MS(+ES), m/z: 176 (M+H)$^+$.

EXAMPLE 7

3-Dimethylamino-1-phenyl-2-propene-1-one

A solution of 1-dimethylarmmino-3-phenyl-2-propyne N-oxide (250 mg) in methanol (20 ml) was heated to reflux for 5 hours. The mixture was cooled, the solvent was evaporated in vacuo, and the desired product was obtained as a nearly colorless solid by chromatography of the remaining residue over silica gel (2:1 ethyl acetate-hexanes was used as the eluant). MS(+ES), m/z: 176 (M+H)$^+$. The purified product was identical by $^1$H NMR and thin layer chromatography to material prepared by the known reaction of 1-phenyl-prop-2-yne-1-one with dimethylamine; McMullen,et.al. *J. Chem. Soc.*(B) 1966, 1217; Hirao, I. *J. Chem. Soc. Japan* 1953, 56, 968 (*Chem. Abs.* 1955, 3185f).

EXAMPLE 8

3-Dimethylamino-1-phenyl-2-propene-1-one

To a solution of 1-dimethylamino-3-phenyl-2-propyne N-oxide (50 mg) in methanol (1 ml) was added bis(acetonitrile)palladium(II) chloride (7.5 mg) and the mixture was stirred at room temperature under an atmosphere of argon for 24 hours. The mixture was diluted with ethyl acetate, washed with saturated aqueous sodium chloride, and the organic layer was dried over anhydrous magnesium sulfate. The solvent was removed by evaporation in vacuo. The residue was chromatographed over silica gel (eluted with 2:1 ethyl acetate-hexanes) to give upon evaporation of the solvent in vacuo the desired product as a nearly colorless solid. MS(+ES), m/z: 176 (M+H)$^+$. The purified product was identical by $^1$H NMR and thin layer chromatography to material prepared by the known reaction of 1-phenyl-prop-2-yne-1-one with dimethylamine; McMullen,et.al. *J. Chem. Soc.*(B) 1966, 1217; Hirao, I. *J. Chem. Soc. Japan* 1953, 56, 968 (*Chem. Abs.* 1955, 3185f).

EXAMPLE 9

3-Dimethylamino-1-phenyl-2-propene-1-one

To a solution of 1-dimethylamino-3-phenyl-2-propyne N-oxide (50 mg) in methanol (1 ml) was added cuprous iodide (5.5 mg) and the mixture was stirred at room temperature under an atmosphere of argon for 4 days. The mixture was diluted with ethyl acetate, washed with saturated aqueous sodium chloride, and the organic layer was dried over anhydrous magnesium sulfate. The solvent was removed by evaporation in vacuo and the residue was chromatographed over silica gel (eluted with 2:1 ethyl acetate-hexanes) to give upon evaporation of the solvent in vacuo the desired product as a nearly colorless solid. MS(+ES), m/z: 176 (M+H)$^+$. The purified product was identical by $^1$H NMR and thin layer chromatography to material prepared by the known reaction of 1-phenyl-prop-2-yne-1-one with dimethylamine; McMullen,et.al. *J. Chem. Soc.*(B) 1966, 1217; Hirao, I. *J. Chem. Soc. Japan* 1953, 56, 968 (*Chem. Abs.* 1955, 3185f).

EXAMPLE 10

3-Dimethylamino-1-phenyl-2-propene-1-one

To a solution of 1-dimethylamino-3-phenyl-2-propyne N-oxide (50 mg) in a biphasic solution of dichloromethane-water (1:1, 2 ml) was added benzyldimethyltetradecylammonium chloride dihydrate (approximately 1 mg) and bis(acetonitrile)palladium(II) chloride (3.8 mg) and the mixture was stirred vigorously for 24 hours. The reaction was diluted with ethyl acetate, washed with saturated aqueous sodium chloride, and the organic layer was dried over anhydrous magnesium sulfate. The solvent was removed by evaporation in vacuo and the residue was chromatographed over silica gel (eluted with 2:1 ethyl acetate-hexanes) to give upon evaporation of the solvent in vacuo the desired product as a nearly colorless solid. MS(+ES), m/z: 176 (M+H)$^+$. The purified product was identical by $^1$H NMR and thin layer chromatography to material prepared by the known reaction of 1-phenyl-prop-2-yne-1-one with dimethylamine; McMullen,et.al. *J. Chem. Soc.*(B) 1966, 1217; Hirao, I. *J. Chem. Soc. Japan* 1953, 56, 968 (*Chem. Abs.* 1955, 3185f).

EXAMPLE 11

3-Dimethylamino-1-phenyl-2-propene-1-one

To a solution of 1-dimethylamino-3-phenyl-2-propyne N-oxide (50 mg) in a biphasic solution of dichloromethane-water (1:1, 2 ml) was added benzyldimethyltetradecylammonium chloride dihydrate (approximately 1 mg) and cuprous iodide (2.8 mg) and the mixture was stirred vigorously for approximately 24 hours. The reaction was diluted with ethyl acetate, washed with saturated aqueous sodium chloride, and the organic layer was dried over anhydrous magnesium sulfate. The solvent was removed by evaporation in vacuo and the residue was chromatographed over silica gel (eluted with 2:1 ethyl acetate-hexanes) to give upon evaporation of the solvent in vacuo the desired product as a nearly colorless solid. MS(+ES), m/z: 176 (M+H)$^+$. The purified product was identical by $^1$H NMR and thin layer chromatography to material prepared by the known reaction of 1-phenyl-prop-2-yne-1-one with dimethylamine; McMullen,et.al. *J. Chem. Soc.*(B) 1966, 1217; Hirao, I. *J. Chem. Soc. Japan* 1953, 56, 968 (*Chem. Abs.* 1955, 3185f).

EXAMPLE 12

4-Dimethylamino-1-phenyl-3-butene-2-one

To an ice cold solution of 1-dimethylamino-4-phenyl-2-butyne (0.5 g; prepared by the Mannich reaction of 3-phenyl-1-propyne with formaldehyde and dimethylamine as per Mornet, et.al. *Bull.Soc.Chim.Fr.* 1974, 206) in dichloromethane (12 ml) was added in small portions 3-chloroperoxybenzoic acid (0.52 g). After the reaction was stirred at 0° C. for 20 minutes, the mixture was passed over twenty weight equivalents of basic alumina (Brockmann Grade I, 150 mesh) and the N-oxide was eluted using a solution of 10% methanol in dichloromethane. All fractions containing the desired amine N-oxide were combined and evaporated to near dryness in vacuo. The residue was treated successively three times with small portions of methanol (ca. 10 ml) followed by evaporation to near dryness, and the volume of the solution was adjusted to 25 mL by addition of methanol. The methanolic solution of the N-oxide was heated to reflux for approximately 4 hours and cooled. The solvent was evaporated to dryness in vacuo and the residue was chromatographed over silica gel (95:5 ethyl acetate-hexanes was used as the eluant) to give upon evaporation of the solvent in vacuo the desired product as an oil. MS(+ES) m/z: 190 (M+H)$^+$.

EXAMPLE 13

1-Dimethylamino-1-pentene-3-one

To an ice cold solution of 1-dimethylamino-2-pentyne (3.0 g) in dichloromethane (100 ml) was added 3-chloroperoxybenzoic acid (4.66 g) in small portions. After the reaction was stirred at 0° C. for 20 minutes, the mixture was passed over twenty weight equivalents of basic alumina (Brockmann Grade I, 150 mesh) and the N-oxide was eluted using a solution of 5% methanol in dichloromethane. All fractions containing 1-dimethylamino-2-pentyne N-oxide were combined and evaporated to near dryness in vacuo. The residue was treated successively three times with of methanol (ca. 100 ml) followed by evaporation to near dryness, and the volume of the solution was adjusted to 90 mL by addition of methanol. One third of this methanolic solution (30 ml) of the N-oxide (9 mmol) was heated to reflux for approximately 4 hours, cooled, evaporated to dryness in vacuo, and the residue was chromatographed over silica gel (2% methanol in dichloromethane was used as the eluant) to give upon evaporation of the solvent in vacuo the desired product as an oil. MS (+ES) m/z: 128 (M+H)$^+$

EXAMPLE 14

1-Dimethylamino-1-pentene-3-one

To a solution of 1-dimethylamino-2-pentyne N-oxide (1 g) in methanol (30 ml) was added bis(acetonitrile)palladium (II) chloride (117 mg) and the mixture was stirred at room temperature under an atmosphere of argon for 24 hours. The mixture was evaporated to dryness in vacuo, and the residue was chromatographed over silica gel (2% methanol in dichloromethane was used as the eluant) to give upon evaporation of the solvent in vacuo the desired product as an oil. MS (+ES) m/z: 128 (M+H)$^+$

EXAMPLE 15

1-Dimethylamino-1-pentene-3-one

To a solution of 1-dimethylarino-2-pentyne N-oxide (1 g) in methanol (30 ml) was added cuprous iodide (86 mg) and the mixture was stirred at room temperature under an atmosphere of argon for 24 hours. The mixture was evaporated to dryness in vacuo, and the residue was chromatographed over silica gel (2% methanol in dichloromethane was used as the eluant) to give upon evaporation of the solvent in vacuo the desired product as an oil. MS (+ES) m/z: 128 (M+H)$^+$

EXAMPLE 16

4-Bromo-2-chloro-benzoic acid, methyl ester

Thionyl chloride (1.64 ml) was added dropwise to a suspension of 4-bromo-2-chlorobenzoic acid (6.92 g) in methanol, and heated to 60 ° C. for 2 hours. The solvent was removed in vacuo, the residue redissolved in ethyl acetate, and washed sequentially with 0.5 N sodium hydroxide (2×), water, and brine. The organic phase was dried over anhydrous sodium sulfate, and the solvent removed in vacuo to afford upon evaporation of the solvent in vacuo 7.8 g of the title compound as an oil. $^1$H NMR (300 Mhz), d: 3.87 (s,3H), 7.68–7.9 (m, 3H).

EXAMPLE 17

2-Chloro-4-(3-dimethylamino-propyn-1-yl)benzoic acids methyl ester

To a stirred solution of 4-bromo-2-chlorobenzoic acid methyl ester (18.69 g) in triethylamine (110 ml), was added 1-dimethylamino-2-propyne (12.1 ml), bis(triphenylphosphine)palladium(II) chloride (1.26 g), and copper(I) iodide (0.136 g). The mixture was heated slowly to 60 ° C., and the temperature maintained for one hour. The reaction was cooled to room temperature, filtered through diatomaceous earth, and the collected solid washed with ethyl acetate. The solvent was removed in vacuo, the resulting residue redissolved in ethyl acetate, and washed with water (3×). The combined organic extract was dried over anhydrous sodium sulfate, and the solvent removed in vacuo to give a crude product. The crude product was purified by column chromatography over silica gel (225 g), eluting with 40% ethyl acetate/hexane. Removal of the solvent in vacuo gave the title compound (17.7 g) as a viscous oil. MS (+FAB), m/z : 252 (M+H)$^+$.

EXAMPLE 18

2-Chloro-4-(3-dimethylamino-2-propen-1-on-1-yl)-benzoic acids methyl ester

To a pre-cooled solution of 2-chloro-4-(3-dimethylammnino-propyn-1yl)-benzoic acid, methyl ester (15.07 g) at −20 ° C. in dichloromethane (40 ml), was gradually added 3-chloroperoxybenzoic acid (10.76 g), while maintaining the reaction temperature at −20° C. The mixture was stirred for 10–15 minutes. The resulting N-oxide was purified by chromatography on Activity Grade I basic alumina (215 g), eluting with 10% methanol/dichloromethane. The solvent was evaporated in vacuo between 12 to 18° C. The resulting residue was dissolved in methanol (100 ml) and heated at 60–65° C. with stirring for 18 hours. After removing the solvent in vacuo, and the product was purified by column chromatography over silica gel (190 g), eluting with 70% ethyl acetate/hexane. Trituration with diethyl ether containing some hexanes afforded the title compound (5.68 g) as a solid. m.p. 92–96° C.

EXAMPLE 19

2-Chloro-4-(1H-pyrazol-3-yl)-benzoic acid, methyl ester

To a suspension of 2-chloro-4-(3-dimethylamino-2-propen-1-on-1-yl)-benzoic acid, methyl ester (13.67 g) in ethanol (53 ml) was added hydrazine monohydrochloride (7.0 g). The mixture was heated in an oil bath at 75–80° C. for one hour. The solvent was removed in vacuo. The resulting residue was dissolved in ethyl acetate, washed with water and brine, dried over anhydrous sodium sulfate, and the solvent removed in vacuo to yield the title compound as a crude solid (12 g). A purified sample had a melting point of 130–131° C.

EXAMPLE 20

2-Chloro-4-(1-methyl-1H-pyrazol-3-yl)-benzoic acid, methyl ester

To a suspension of hexanes-washed sodium hydride (3.05 g, 60% dispersion) in dimethylformamide (6 ml) under nitrogen was added a solution of 2-chloro-4-(1H-pyrazol-3yl)-benzoic acid methyl ester (12.0 g) in dimethylformamide (30 ml) over a period of 15 minutes. The mixture was stirred at room temperature for 30 minutes. Iodomethane (9.5 ml) was added dropwise over 15 minutes. The mixture was allowed to stir at room temperature for 45 minutes. Additional iodomethane (5.16 ml) was added, and the reaction stirred another 75 minutes. The reaction was diluted with a small quantity of water, and concentrated in vacuo. The residue was diluted with water (500 ml) and extracted five times with ethyl acetate. The combined organic phase was evaporated in vacuo to afford a crude product, which was purified by column chromatography over silica gel (15% ethyl acetate-hexanes was used as the eluant) to give pure fractions of 1-methyl regioisomer (4.29 g), and a mixture of the 1-methyl and 2-methyl regioisomers (4.6 g). The mixture of isomers was triturated with hexanes three times to give an additional sample of the pure 1-methyl regioisomer (2.55 g), m.p. 66.5–67° C.; MS (+FAB), m/z:: 251 (M+H)+.

EXAMPLE 21

2-Chloro-4-(1-methyl-1H-pyrazol-3-yl)-benzoic acid

To a solution of 2-chloro-4-(1-methyl-1H-pyrazol-3-yl)-benzoic acid, methyl ester (6.85 g) in methanol (32 ml) was added 2.5N sodium hydroxide solution (15.3 ml). The reaction was heated to 50° C. for one hour. The solvent was removed in vacuo, and the residue dissolved in water (250 ml), cooled in an ice bath, and acidified with 2N hydrochloric acid (24 ml). The resulting precipitate was filtered and dried to give a colorless solid (6.3 g) m.p. 232–233° C.; MS, (+FAB), m/z: 236 (M+H)+.

EXAMPLE 22

[2-Chloro-4-(1-methyl-1H-pyrazol-3-yl)-phenyl]-(5H,11H-pyrrolo[2,1-c] [1,4]benzodiazepine-10-yl)-methanone Well powdered 2-chloro-4-(1-methyl-1H-pyrazol-3-yl)-benzoic acid (6.3 g) and dimethylformamide (2.16 ml) were suspended under nitrogen in a mixture of tetrahydrofuran (70 ml) and dichlormethane (15 ml). A solution of oxalyl chloride (2.43 ml) in dichloromethane (5 ml) was added dropwise, and the reaction stirred for one hour. The resulting suspension of 2-chloro-4-(1-methyl-1H-pyrazol-3-yl)-benzoyl chloride was utilized without further purification.

To a suspension of 10,11-dihydro-5H-pyrrolo[2,1-c][1,4] benzodiazepine (4.93 g) in dichloromethane (15 ml) was added diisopropylethylamine (7 ml). The suspension of the freshly prepared acid chloride was gradually added over 15 minutes under a positive flow of nitrogen. The slightly warm reaction mixture was stirred under nitrogen for 50 minutes. After stirring one hour, the mixture was concentrated in vacuo. The residue was dissolved in dichloromethane, washed with water, 5% aqueous sodium bicarbonate, and water. The organic phase was washed with brine, dried over anhydrous sodium sulfate, and the solvent removed in vacuo to give a crude product, which was purified by column chromatography over silica gel (30–40% ethyl acetate-hexanes was used as the eluant) to afford the product as an oil. Crystallization was induced by stirring the oil with diethyl ether containing hexanes for 24 hours. Filtration of the precipitate afforded the title compound as a crystalline solid. m.p. 148.5–150° C.; MS (EI), m/z: 402 (M)+.

EXAMPLE 23

[2-Chloro-4-(1-methyl-1H-pyrazol-3-yl)-phenyl]-(5,11-dihydro-pyrido[2,3-b][1,5]benzodiazepin-6-yl)-methanone Step A. 6,11-Dihydro-5H-pyrido[2,3-b][1,5]benzodiazepin-5-one 1:1 salt with hydrochloric acid A mixture of 1,2-phenylene diamine (52 g, 480 mmol) and chloro nicotinic acid (76 g, 482 mmol) in cyclohexanol (480 mL) was refluxed under nitrogen for 2.5 hours. A precipitate appeared soon after the heating was initiated. The warm reaction mixture was carefully poured onto ice-cold dichloromethane (1000 mL) under vigorous stirring. The semisolid mass was collected, washed thoroughly with dichloromethane and dried in vacuo to yield 98.9 g (83%) of the title compound which was used in the next step without further purification.

Step B. 6,11-Dihydro-5H-pyrido[2,3-b][1,5]benzodiazepine

Diborane dimethylsulfide complex (35 mL) was added via syringe to a suspension of 6,11-dihydro-5H-pyrido[2,3-b] [1,5]benzodiazepin-5-one 1:1 salt with hydrochloric acid of Step A (25 g, 0.1 mole) in dioxane (230 mL) under nitrogen. The mixture was sonicated overnight at room temperature and then evaporated to dryness in vacuo. The green residue was treated with cold 2N hydrochloric acid and diethyl ether. The cold aqueous layer was basified with 50% aqueous sodium hydroxide (to pH 9) and the basic layer extracted with ethyl acetate. The organic extracts were dried over anhydrous potassium carbonate, and evaporated to dryness to yield a burgundy solid (24.35 g, 61.4%). This crude material was purified by trituration with diethyl ether. The solid was collected, washed and dried in vacuo. The mother liquors from different runs were combined and the mixture (18.5 g) flash chromatographed (on silica Merck-60, eluant 20% ethyl acetate in hexane) to provide additional material homogeneous by TLC (yellow solid, 11 g).

Step C. [2-Chloro-4-(1-methyl-1H-pyrazol-3-yl)-phenyl]-(5,11-dihydropyrido- [2,3-b][1,5]benzodiazepin-6-yl)-methanone A mixture of 2-chloro-4-(1-methyl-1H-pyrazol-3-yl)-benzoic acid (1.9 g) and oxalyl chloride (0.79 mL) in dichloromethane (20 ml) containing a catalytic amount of dimethylformamide (0.01 ml) was stirred at ambient temperature under an atmosphere of nitrogen for 1 hour. The solvent was removed by evaporation in vacuo and the resulting crude solid acid chloride was dissolved in of dimethylformamide (5 ml) and added directly to a mixture of 5,11-dihydro-pyrido[2,3-b][1,5]benzodiazepine (1.59 g) and potassium carbonate (1.25 g). After stirring for 2 hours at room temperature the reaction mixture was partitioned between ethyl acetate and water. The organic phase was washed with water and brine. After drying over anhydrous sodium sulfate, the solvent was removed by evaporation in vacuo and the product was purified by chromatography over silica gel (a linear gradient of 57% to 66% ethyl acetate in hexanes was used as the eluant) and recrystallized from ethanol-ether giving colorless solids. m.p. 202° C.

EXAMPLE 24

(3-Chloro-4-iodo-phenyl)-carbamic acid tert-butyl ester

To a solution of 3-chloro4-iodoaniline (20.2 g) in tetrahydrofuran (200 ml) was added di-tert-butyl dicarbonate (39 g) and N,N-diisopropylethylamine (30.9 g). The mixture was heated to reflux for approximately 24 hours, cooled and the solvent removed by evaporation in vacuo. The resulting residue was dissolved in ethyl acetate (450 ml), washed twice with of 5% aqueous hydrochloric acid, once with saturated aqueous sodium bicarbonate, once with water, once with saturated sodium chloride, and dried over anhydrous magnesium sulfate. The solvent was removed by evaporation in vacuo, and trituration of the product with hexanes gave the product as a crystalline solid. MS (–ES) m/z: 352 (M–H)_. Additional purification was accomplished by recrystallization from hot hexanes.

EXAMPLE 25

[3-Chloro-4-(3-dimethylamino-prop-1-ynyl)-phenyl]-carbamic acid tert-butyl ester To a deoxygenated solution of (3-chloro-4-iodo-phenyl)-carbamic acid tert-butyl ester (10.0 g) in triethylamine (120 ml) was added 1-dimethylamino-2-propyne (2.82 g), bis (triphenylphosphine)palladium(II) chloride (400 mg), and cuprous iodide (54 mg). The mixture was stirred at room temperature under an atmosphere of argon for approximately 6 hours, heated briefly (ca. 10 minutes) to 60° C. The reaction mixture was cooled, filtered through diatomaceous earth, and the solvent was removed by evaporation in vacuo. The residue was dissolved in ethyl acetate, washed three times with water, once with saturated aqueous sodium chloride, and dried over anhydrous magnesium sulfate. The solvent was removed by evaporation in vacuo, and the residue was purified by chromatography over silica gel (80% ethyl acetate in hexanes was used as the eluant) to give the product as an amber oil that solidified on standing. MS (+ES) m/z: 309 (M+H)$^+$.

EXAMPLE 26

[3-Chloro-4-(3-dimethylamino-2-propen-1-on-1-yl)-phenyl]-carbamic acid tert-butyl ester To an ice cold solution of [3-chloro-4-(3-dimethylamino-prop-1-ynyl)-phenyl]-carbammic acid tert-butyl ester (4.0 g) in dichloromethane (30 ml) was added in small portions 3-chloroperoxybenzoic acid (2.34 g). After the reaction was stirred at 0° C. for 20 minutes, the mixture was passed over twenty weight equivalents of basic alumina (Brockmann Grade I, 150 mesh) and the N-oxide was eluted using a solution of 5% methanol in dichloromethane. All fractions containing the desired amine N-oxide were combined and evaporated to near dryness in vacuo. The residue was treated successively three times with small portions of methanol (ca. 50 ml) followed by evaporation to near dryness, and the volume of the solution was adjusted to 250 mL by addition of methanol. The methanolic solution of the N-oxide was heated to reflux for approximately 15 hours, cooled, and the solvent was evaporated to dryness in vacuo. The residue was purified by chromatography over silica gel (80% ethyl acetate in hexanes was used as the eluant) to give the desired product as pale yellow solids. MS (+ES) m/z: 325 (M+H)$^+$.

EXAMPLE 27

2-Methyl-5-(pyrrolidin-1-yl)-pent-3-yn-2-ol

A solution of 1-(pyrrolidin-1-yl)-prop-2-yne (prepared by the method of Biel and DiPierro *J. Am. Chem. Soc.* 1958, 80, 4609) (0.545 g) in dry tetrahydrofuran (15 ml) was treated at –78° C. with a solution of n-butyl lithium in hexanes (2.5 M, 2.2 ml) and the mixture was allowed to stir at –78° C. for 30 minutes and them permitted to warm to room temperature over the course of one hour. Upon recooling to –78° C. this mixture was treated with a solution of acetone (1 ml) in tetrahydrofuran (1 ml). The reaction was permitted to warm to room temperature over the course of two hours, and was then partitioned between ethyl acetate and water. The aqueous layer was extracted with ethyl acetate, and the pooled organic phase was washed with water, brine, and then dried over anhydrous sodium sulfate. The solvent was removed in vacuo to give a crude product, which was purified by column chromatography over silica gel (5% methanol in dichloromethane was used as the eluant) to afford the product as an oil. MS(+ES), m/z: 168 (M+H)$^+$.

EXAMPLE 28

4-Hydroxy-4-methyl-1-(pyrrolidin-1-yl)-pent-1-en-3-one

To an ice cold solution of 2-methyl-5-(pyrrolidin-1-yl)-pent-3-yn-2-ol (0.25 g) in dichloromethane (6 ml) was added in small portions 3-chlorophenylperoxybenzoic acid (0.285 g) over a period of about 2 minutes. After the reaction was stirred at 0° C. for 5 minutes, the mixture was passed over 20 weight equivalents of basic alumina (Brockmann Grade I, 150 mesh) and eluted with 5% methanol in dichloromethane. All fractions containing the desired amine N-oxide were combined and evaporated to near dryness in vacuo. The resulting residue was dissolved in methanol (20 ml) and heated to reflux temperatures for 7 hours. The solvent was then removed in vacuo and the residue was chromatographed over silica gel (50% ethyl acetate in hexanes was used as the eluant) to provide the desired product as an amber solid. MS(+ES), m/z: 184 (M+H)$^+$.

EXAMPLE 29

2.2-Dimethyl-3(2H)-furanone

A solution of 4-hydroxy-4-methyl-1-(pyrrolidin-1-yl)-pent-1-en-3-one (0.075 g) in methanol (1 ml) was treated with p-toluene sulfonic acid (0.015 g) and the mixture was stirred at room temperature for approximately 15 hours. The solution was then diluted with diethyl ether, washed with water, 5% aqueous hydrochloric acid, saturated aqueous sodium bicarbonate, brine, and then dried over anhydrous magnesium sulfate. The solvent was carefully removed to provide the desired product as an oil, which was identical by $^1$H NMR and thin layer chromatography to commercially available material obtained from the Aldrich Chemical Company.

EXAMPLE 30

1-(3-(Pyrrolidin-1-yl)-prop-1-ynyl)-cyclohexanol

A solution of 1-(pyrrolidin-1-yl)-prop-2-yne (prepared by the method of Biel and DiPierro *J. Am. Chem. Soc.* 1958, 80, 4609) (0.545 g) in dry tetrahydrofuran (15 ml) was treated at −78° C. with a solution of n-butyl lithium in hexanes (2.5 M, 2.2 ml) and the mixture was allowed to stir at −78° C. for 30 minutes and them permitted to warm to room temperature over the course of one hour. Upon recooling to −78° C. this mixture was treated with a solution of cyclohexanone (0.61 g) in tetrahydrofuran (1 ml). The reaction was permitted to warm to room temperature over the course of two hours, and was then partitioned between ethyl acetate and water. The aqueous layer was extracted with ethyl acetate, and the pooled organic phase was washed with water, brine, and then dried over anhydrous sodium sulfate. The solvent was removed in vacuo to give a crude product, which was purified by column chromatography over silica gel (5% methanol in dichloromethane was used as the eluant) to afford the product as a white solid. MS(+ES), m/z: 208 (M+H)$^+$.

EXAMPLE 31

1-(1-Hydroxy-cyclohexyl)-3-(pyrrolidin-1-yl)-propenone

To an ice cold solution of 1-(3-(pyrrolidin-1-yl)-prop-1-ynyl)-cyclohexanol (0.31 g) in dichloromethane (6 ml) was added in small portions 3-chlorophenylperoxybenzoic acid (0.285 g) over a period of about 2 minutes. After the reaction was stirred at 0° C. for 5 minutes, the mixture was passed over 20 weight equivalents of basic alumina (Brockmann Grade I, 150 mesh) and eluted with 5% methanol in dichloromethane. All fractions containing the desired amine N-oxide were combined and evaporated to near dryness in vacuo. The resulting residue was dissolved in methanol (20 ml) and heated to reflux temperatures for 7 hours. The solvent was then removed in vacuo and the residue was chromatographed over silica gel (50% ethyl acetate in hexanes was used as the eluant) to provide the desired product as an amber solid. MS(+ES), m/z: 224 (M+H)$^+$.

EXAMPLE 32

1-Oxa-spiro[4.5]dec-2-en-4-one

A solution of 1-(1-hydroxy-cyclohexyl)-3-(pyrrolidin-1-yl)-propenone (0.11 g) in methanol (1 ml) was treated with p-toluene sulfonic acid (0.015 g) and the mixture was stirred at room temperature for approximately 15 hours. The solution was then diluted with diethyl ether, washed successively with water, 5% aqueous hydrochloric acid, saturated aqueous sodium bicarbonate, brine, and then dried over anhydrous magnesium sulfate. The solvent was removed in vacuo and the residue was chromatographed over silica gel (15% ethyl acetate in hexanes was used as the eluant) to provide the desired product as a colorless oil. MS (CI), m/z: 153 (M+H)$^+$.

EXAMPLE 33

2-(Pyrrolidin-1-yl)-but-3-yne

A solution acetic acid 1-methyl-prop-2-ynyl ester (prepared by the method of Clarke and Pinder, *J. Chem. Soc.* 1958, 1967).(7 g) and pyrrolidine (10.4 ml) in anhydrous tetrahydrofuran (125 ml) was treated with copper (I) chloride (0.3 g) and the mixture was heated to reflux temperatures for 1.5 hours. After then allowing the mixture to stir at room temperature for approximately 15 hours, the mixture was diluted with diethyl ether, and extracted thrice with 2N aqueous hydrochloric acid. These pooled acidic extracts were basified by addition of solid sodium hydroxide, and the solution was then extracted three times with ethyl acetate. These pooled organic extracts were then washed with water, brine, and dried over anhydrous magnesium sulfate. After removing the solvent in vacuo the resulting residue was distilled to obtain the desired product as a colorless oil. b.p. 35° C. (1.1 mm Hg). MS(+ES), m/z: 124 (M+H)$^+$.

EXAMPLE 34

2-Phenyl-5-(pyrrolidin-1-yl)-hex-3-yn-2-ol

A solution of 2-(pyrrolidin-1-yl)-but-3-yne (0.1.23 g) in dry tetrahydrofuran (20 ml) was treated at −78° C. with a solution of n-butyl lithium in hexanes (2.5 M, 4.4 ml) and the mixture was allowed to stir at −78° C. for 30 minutes and them permitted to warm to room temperature over the course of one hour. Upon recooling to −78° C. this mixture was treated with a solution of acetophenone (1.2 g) in tetrahydrofuran (5 ml). The reaction was permitted to warm to room temperature over the course of two hours, and was then partitioned between ethyl acetate and water. The aqueous layer was extracted with ethyl acetate, and the pooled organic phase was washed with water, brine, and then dried over anhydrous sodium sulfate. The solvent was removed in vacuo to give a crude product, which was purified by column chromatography over silica gel (5–10% methanol in dichloromethane was used as the eluant) to afford the product as an oil that solidified on standing. MS(+ES), m/z: 244 (M+H)⁺.

EXAMPLE 35

4-Hydroxy-4-phenyl-1-(pyrrolidin-1-yl)-pent-1-en-3-one

To an ice cold solution of 2-phenyl-5-(pyrrolidin-1-yl)-hex-3-yn-2-ol (0.49 g) in dichloromethane (5 ml) was added in small portions 3-chlorophenylperoxybenzoic acid (0.38 g) over a period of about 2 minutes. After the reaction was stirred at 0° C. for 5 minutes, the mixture was passed over 20 weight equivalents of basic alumina (Brockmann Grade I, 150 mesh) and eluted with 5% methanol in dichloromethane. All fractions containing the desired amine N-oxide were combined and evaporated to near dryness in vacuo. The resulting residue was dissolved in methanol (20 ml) and heated to reflux temperatures for 13 hours. The mixture was then cooled and the solvent removed in vacuo. The resulting residue consisted of 4-hydroxy-4-phenyl-1-pyrrolidin-1-yl-pent-1-en-3-one and 2,5-dimethyl-2-phenyl-furan-3-one, and was used directly and without further purification in the next step (Example 36).

EXAMPLE 36

2.5-Dimethyl-2-phenyl-furan-3-one

The mixture prepared above (Example 35) of 4-hydroxy-4-phenyl-1-(pyrrolidin-1-yl)-pent-1-en-3-one and 2,5-dimethyl-2-phenyl-furan-3-one was dissolved in methanol (20 ml) and stirred 4 hours in the presence of Amberlyst® (0.5 g) The mixture was then filtered and the solvent was then removed in vacuo and the residue was chromatographed over silica gel (20% ethyl acetate in hexanes was used as the eluant) to provide the desired product as an oil. The compound was identified by comparison of the ¹H NMR with authentic material prepared by the method of Felman, Jirkovsky, Memoli, Borella, Wells, Russell, and Ward *J. Med. Chem.* 1992, 35, 1183.

EXAMPLE 37

2-(3-Dimethylamino-prop-1-ynyl)-phenol

To a deoxygenated solution of o-bromophenol (10.0 g) in triethylamine (120 ml) may be added 1-dimethylamino-2-propyne (2.82 g), bis(triphenylphosphine)palladium(II) chloride (400 mg), and cuprous iodide (54 mg). The mixture may be stirred at room temperature under an atmosphere of argon for approximately 6 hours, heated briefly (ca. 10 minutes) to 60° C. The reaction mixture is then cooled, filtered through diatomaceous earth, and the solvent may be removed by evaporation in vacuo. The residue can then be dissolved in ethyl acetate, washed three times with water, once with saturated aqueous sodium chloride, and dried over anhydrous magnesium sulfate. The solvent may be removed by evaporation in vacuo, and the residue may be purified by chromatography over silica gel (50% ethyl acetate in hexanes may be used as the eluant) to give the purified product.

EXAMPLE 38

2-(1-(3-Dimethylamino-prop-2-en-1-one))-phenol

To an ice cold solution of 2-(3-dimethylamino-prop-1-ynyl)-phenol (4.0 g) in dichloromethane (30 ml) can be added in small portions 3-chloroperoxybenzoic acid (2.34 g). After the reaction is stirred at 0° C. for 20 minutes, the mixture can be passed over twenty weight equivalents of basic alumina (Brockmann Grade I, 150 mesh) and the N-oxide can be eluted using a solution of 5% methanol in dichloromethane. All fractions containing the desired amine N-oxide can be combined and evaporated to near dryness in vacuo. The residue can be treated successively three times with small portions of methanol (ca. 50 ml) followed by evaporation to near dryness, and the volume of the solution can be adjusted to 250 mL by addition of methanol. The methanolic solution of the N-oxide can be heated to reflux for approximately 15 hours, and then cooled to provide a mixture of 2-(1-(3-dimethylamino-prop-2-en-1-one))-phenol and chromone (1,4-Benzopyrone), which can be used directly and without further purification in the next step (Example 39).

EXAMPLE 39

Chromone or 1,4-Benzopyrone

The mixture prepared above (Example 38) of 2-(1-(3-dimethylamino-prop-2-en-1-one))-phenol and chromone may be dissolved in methanol (20 ml) and stirred in the presence of Amberlyst® (1 g) for 4 hours. After removing the solvent in vacuo, the residue can be purified by chromatography over silica gel (25% ethyl acetate in hexanes can be used as the eluant) to give the desired chromone product.

What is claimed:
1. A process for producing an enaminone of Formula (I):

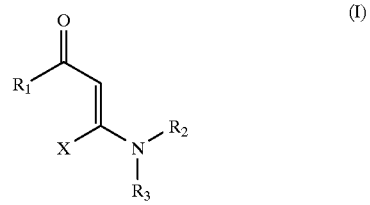

wherein:

X is selected from the group of H, $C_1$–$C_6$ straight chain aikyl, $C_3$–$C_6$ branched chain alkyl, $C_3$–$C_7$ cycloalkyl, —$CH_2$-phenyl, or —$CH_2$-substituted phenyl;

$R_1$ is selected from the group of hydrogen, $C_1$–$C_6$ straight chain alkyl, $C_3$–$C_6$ branched chain alkyl, $C_3$–$C_7$ cycloalkyl, phenyl, substituted phenyl, —$CH_2$-phenyl, or —$CH_2$-substituted phenyl or a group of the formulae:

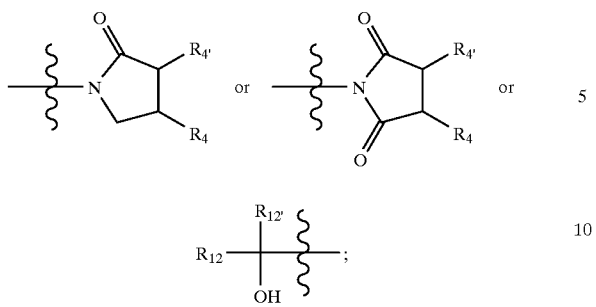

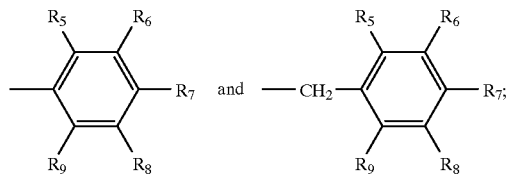

the $C_3$–$C_7$ cycloalkyl groups being optionally substituted by from 1 to 3 groups independently selected from $R_5$–$R_9$;

$R_2$ and $R_3$ are independently selected from the group of $C_1$–$C_6$ straight chain alkyl, $C_3$–$C_6$ branched chain alkyl, $C_3$–$C_7$ cycloalkyl, —$CH_2$-phenyl, or $R_2$ and $R_3$ may be joined to form a ring of from three to six atoms;

$R_4$ and $R_{4'}$ are independently selected from the group of hydrogen, $C_1$–$C_6$ straight chain alkyl, $C_3$–$C_6$ branched chain alkyl, $C_3$–$C_7$ cycloalkyl, —$OR_{11}$, —$NR_{11}R_{13}$, —$NR_{11}C(O)OR_{10}$, —$NR_{11}C(O)R_{10}$, —$OC(O)R_{10}$, —$OC(O)OR_{10}$, or —$OC(O)NHR_{10}$;

Substituted phenyl and —$CH_2$-substituted phenyl are, respectively:

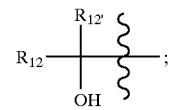

$R_5$–$R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)OR_{11'}$, —$NR_{11}C(O)R_{11'}$, —$OC(O)R_{11}$, —$OC(O)OR_{11}$, or —$OC(O)NHR_{11}$;

$R_{10}$ is selected from the group of hydrogen, $C_1$–$C_{10}$ straight chain alkyl, $C_3$–$C_{10}$ branched chain alkyl, $C_3$–$C_7$ cycloalkyl, phenyl, or —$CH_2$-phenyl;

$R_{11}$ and $R_{11'}$ are independently selected from the group of hydrogen, $C_1$–$C_6$ straight chain alkyl, $C_3$–$C_6$ branched chain alkyl, $C_3$–$C_7$ cycloalkyl, phenyl, or —$CH_2$-phenyl;

$R_{12}$ and $R_{12'}$ are independently selected from the group of hydrogen, $C_1$–$C_6$ straight chain alkyl, $C_3$–$C_6$ branched chain alkyl, $C_3$–$C_7$ cycloalkyl, phenyl, substituted phenyl, —$CH_2$-phenyl or —$CH_2$-substituted phenyl, the $C_3$–$C_7$ cycloalkyl groups being optionally substituted by from 1 to 3 groups independently selected from $R_5$ to $R_9$; or $R_{12}$ and $R_{12'}$ may also optionally be taken together with their associated carbon to form a carbocyclic ring of from three to seven carbon atoms; with a proviso that both $R_{12}$ and $R_{12'}$ in the moiety:

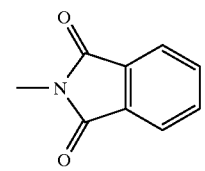

are not both phenyl or substituted phenyl;

$R_{13}$ is an amino-protecting group used to protect the moiety $NR_{11}$; or $NR_{11}R_{13}$ may be optionally concatentated together or exist as a cyclic imide of the formula:

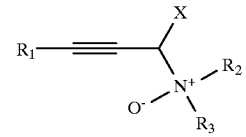

the process comprising converting an amine N-oxide of the formula (II):

$$R_1-\!\!\!\equiv\!\!\!-\underset{\underset{\underset{R_3}{R_2}}{\overset{X}{|}}}{\overset{X}{C}}-\overset{+}{N}\underset{O^-}{}$$ (II)

to the enaminone of the formula I by treating the amine N-oxide with a hydroxylic solvent.

2. The process of claim 1 wherein the $R_{13}$ amino-protecting group is selected from the group of:

(a) acyl type protective groups such as formyl, acetyl, chloroacetyl, dichloroacetyl, trichloroacetyl, trifluoroacetyl, phenylacetyl, o-nitrophenoxyacetyl, sec-butyryl, pivaloyl-(also known as tert-butyryl), cyclopropanoyl, benzoyl, o-nitrobenzoyl, α-chlorobutyryl; or (b) sulfonyl type protecting groups such as benzenesulfonyl, toluenesulfonyl (tosyl), p-methoxybenzenesulfonyl, trifluoromethylsulfonyl; or (c) sufenyl type protecting groups such as benznesulfenyl, o-nitrobenzenesulfenyl, pentachlorobenzenesulfenyl; or (d) urethane type protecting groups such as benzyloxycarbonyl, p-chlorobenzyloxycarbonyl, p-nitrobenzyloxycarbonyl, p-bromobenzyloxycarbonyl, p-methoxybenzyloxycarbonyl, o-nitrobenzyloxycarbonyl, tert-butyloxycarbonyl, tert-amyloxycarbonyl, diisopropylmethoxycarbonyl, isopropyloxycarbonyl, allyloxycarbonyl, cyclopentyloxycarbonyl, adamantyloxycarbonyl, cyclohexyloxycarbonyl, 9-fluorenylmethoxycarbonyl, 2-trimethylsilylethoxycarbonyl; or (e) aralkyl type protecting groups as benzyl, p-methoxybenzyl, p-nitrobenzyl, p-bromobenzyl, or triphenylmethyl.

3. The process of claim 1 wherein —$NR_2R_3$ are joined to form a ring selected from the group of:

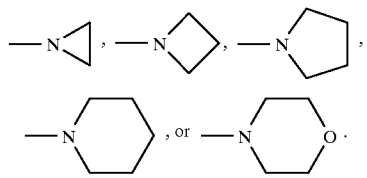

4. The process of claim 1 wherein the hydroxylic solvent is one or more solvents selected from the group of water, $C_1$–$C_8$ straight chain or branched chain alkyl alcohol, ethylene glycol, polyethylene glycol, 1,2-propylene diol, polypropylene glycol, glycerol, 2-methoxyethanol, 2-ethoxyethanol, 2,2,2-trifluoroethanol, benzyl alcohol, or phenol.

5. The process of claim 1 wherein the enaminone is (R)-octylcarbamic acid-1-[4-(dimethylamino)-2-oxo-3-butenyl]-2-oxo-3-pyrrolidinyl ester.

6. The process of claim 1 wherein the enaminone is (R)-1-[4-(dimethylamino)-2-oxo-3-butenyl]-3-hydroxy-2-pyrrolidinone.

7. The process of claim 1 wherein the enaminone is 1-[4-(1-pyrrolidino)-2-oxo-3-butenyl]-2-pyrrolidinone.

8. The process of claim 1 wherein the enaminone is 3-dimethylamino-1-phenyl-2-propene-1-one.

9. The process of claim 1 wherein the enaminone is 1-dimethylamino-1-pentene-3-one.

10. The process of claim 1 wherein the enaminone is 2-chloro-4-(3-dimethylamino-2-propen-1-on-1-yl)-benzoic acid, methyl ester.

11. The process of claim 1 wherein the enaminone is [3-chloro4-(3-dimethylamino-2-propen-1-on-1-yl)-phenyl]-carbamic acid tert-butyl ester.

12. The process of claim 1 wherein the enaminone is 4-Hydroxy-4-methyl-1-pyrrolidin-1-yl-pent-1-en-3-one.

13. The process of claim 1 wherein the enaminone is 1-(1-Hydroxy-cyclohexyl)-3-pyrrolidin-1-yl-propenone.

14. The process of claim 1 wherein the enaminone is 4-Hydroxy-4-phenyl-1-pyrrolidin-1-yl-pent-1-en-3-one.

15. The process of claim 1 wherein the enaminone is 2-(1-(3-Dimethylammnino-prop-2-en-1-one))-phenol.

16. A process for producing an enaminone of Formula (I):

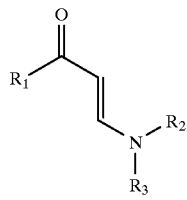

(I)

wherein $R_1$ is selected from the group of $C_1$–$C_6$ straight chain alkyl, $C_3$–$C_6$ branched chain alkyl, $C_3$–$C_7$ cycloalkyl, phenyl, —$CH_2$-phenyl, or the moieties:

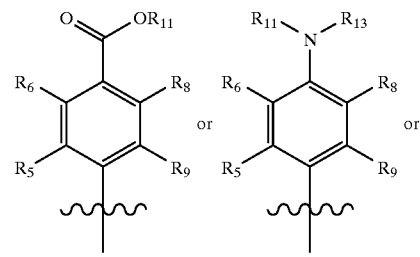

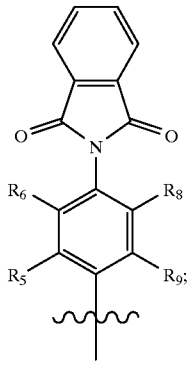

$R_2$ and $R_3$ are independently selected from the group of $C_1$–$C_6$ straight chain alkyl, $C_3$–$C_6$ branched chain alkyl, or $C_3$–$C_7$ cycloalkyl; or $R_2$ and $R_3$ may optionally be joined to form a ring of from three to six atoms;

$R_5$, $R_6$ $R_8$, $R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)OR_{11'}$, —$NR_{11}C(O)R_{11'}$, —$OC(O)R_{11}$, —$OC(O)OR_{11}$, or —$OC(O)NHR_{11}$;

$R_{11}$ and $R_{11'}$ are independently selected from the group of hydrogen, $C_1$–$C_6$ straight chain alkyl, $C_3$–$C_6$ branched chain alkyl, $C_3$–$C_7$ cycloalkyl, phenyl, or —$CH_2$-phenyl;

$R_{13}$ is an amino-protecting group used to transiently protect the moiety $NR_{11}$;

the process comprising converting an amine N-oxide of the formula (II):

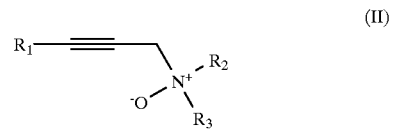

(II)

to the enaminone by treating the amine N-oxide with a hydroxylic solvent.

17. The process of claim 16 wherein —$NR_2R_3$ are joined to form a ring of from three to six atoms selected from the group of:

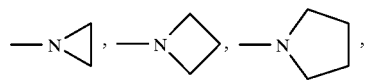

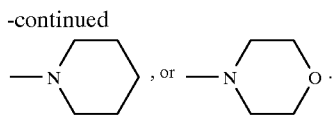

18. The process of claim 16 wherein the amino-protecting group used to transiently protect the moiety $NR_{11}$ is selected from the group of:
   (a) the acyl type protective groups formyl, acetyl, chloroacetyl, dichloroacetyl, trichloroacetyl, trifluoroacetyl, phenylacetyl, o-nitrophenoxyacetyl, sec-butyryl, pivaloyl-(also known as tert-butyryl), cyclopropanoyl, benzoyl, o-nitrobenzoyl, α-chlorobutyryl; or
   (b) the sulfonyl type protecting groups benzenesulfonyl, toluenesulfonyl (tosyl), p-methoxybenzenesulfonyl, trifluoromethylsulfonyl; or
   (c) the sufenyl type protecting groups benznesulfenyl, o-nitrobenzenesulfenyl, pentachlorobenzenesulfenyl; or
   (d) the urethane type protecting groups benzyloxycarbonyl, p-chlorobenzyloxycarbonyl, p-nitrobenzyloxycarbonyl, p-bromobenzyloxycarbonyl, p-methoxybenzyloxycarbonyl, o-nitrobenzyloxycarbonyl, tert-butyloxycarbonyl, tert-amyloxycarbonyl, diisopropylmethoxycarbonyl, isopropyloxycarbonyl, allyloxycarbonyl, cyclopentyloxycarbonyl, adamantyloxycarbonyl, cyclohexyloxycarbonyl, 9-fluorenylmethoxycarbonyl, 2-trimethylsilylethoxycarbonyl.

19. A process for producing an enaminone of Formula (I):

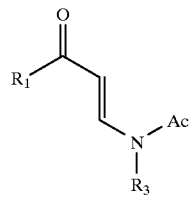

wherein
$R_1$ is the moiety:

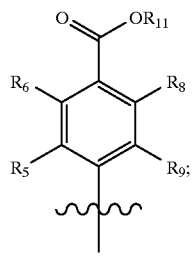

$R_2$ and $R_3$ are independently is selected from the group of $C_1$–$C_6$ straight chain alkyl, $C_3$–$C_6$ branched chain alkyl, or $C_3$–$C_7$ cycloalkyl; or $R_2$ and $R_3$ may optionally be joined to form a ring of from three to six atoms;
$R_5$, $R_6$ $R_8$, $R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)$ $OR_{11'}$, —$NR_{11}C(O)R_{11'}$, —$OC(O)R_{11}$, —$OC(O)OR_{11}$, or —$OC(O)NHR_{11}$;

$R_{11}$ is selected from the group of hydrogen, $C_1$–$C_6$ straight chain alkyl, $C_3$–$C_6$ branched chain alkyl, $C_3$–$C_7$ cycloalkyl, phenyl, or —$CH_2$-phenyl;
$R_{13}$ is an amino-protecting group used to transiently protect the moiety $NR_{11}$; or the moiety $NR_{11}R_{13}$ may optionally exist as a cyclic imide of the formula:

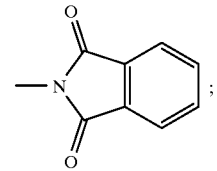

the process comprising converting an amine N-oxide of the formula (II):

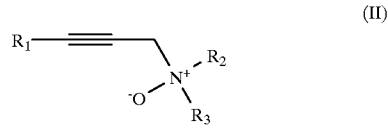

to the enamminone by treating the amine N-oxide with a hydroxylic solvent.

20. The process of claim 19 wherein —$NR_2R_3$ are joined to form a ring of from three to six atoms selected from the group of:

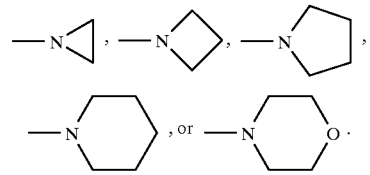

21. The process of claim 19 wherein the amino-protecting group used to transiently protect the moiety $NR_{11}$ is selected from the group of:
   (a) the acyl type protective groups formyl, acetyl, chloroacetyl, dichloroacetyl, trichloroacetyl, trifluoroacetyl, phenylacetyl, o-nitrophenoxyacetyl, sec-butyryl, pivaloyl- (also known as tert-butyryl), cyclopropanoyl, benzoyl, o-nitrobenzoyl, α-chlorobutyryl; or
   (b) the sulfonyl type protecting groups benzenesulfonyl, toluenesulfonyl (tosyl), p-methoxybenzenesulfonyl, trifluoromethylsulfonyl; or
   (c) the sulfenyl type protecting groups benznesulfenyl, o-nitrobenzenesulfenyl, pentachlorobenzenesulfenyl; or
   (d) the urethane type protecting groups benzyloxycarbonyl, p-chlorobenzyloxycarbonyl, p-nitrobenzyloxycarbonyl, p-bromobenzyloxycarbonyl, p-methoxybenzyloxycarbonyl, o-nitrobenzyloxycarbonyl, tert-butyloxycarbonyl, tert-amyloxycarbonyl, diisopropylmethoxycarbonyl, isopropyloxycarbonyl, allyloxycarbonyl, cyclopentyloxycarbonyl, adamantyloxycarbonyl, cyclohexyloxycarbonyl, 9-fluorenylmethoxycarbonyl, 2-trimethylsilylethoxycarbonyl.

22. A process for producing an enaminone of Formula (I):

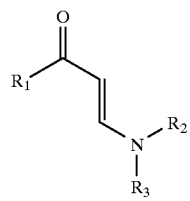
(I)

wherein
$R_1$ is the moiety:

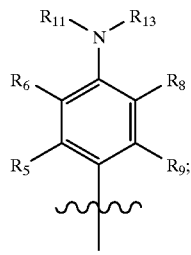

$R_2$ and $R_3$ are independently selected from the group of $C_1$–$C_6$ straight chain alkyl, $C_3$–$C_6$ branched chain alkyl, or $C_3$–$C_7$ cycloalkyl; or $R_2$ and $R_3$ may optionally be joined to form a ring of from three to six atoms;

$R_5$, $R_6$ $R_8$, $R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —NO$_2$, —OR$_{11}$, —CO$_2$R$_{11}$, —NR$_{11}$R$_{13}$, —NR$_{11}$C(O)OR$_{11'}$, —NR$_{11}$C(O)R$_{11'}$, —OC(O)R$_{11}$, —OC(O)OR$_{11}$, or —OC(O)NHR$_{11}$;

$R_{11}$ and $R_{11'}$ are independently selected from the group of hydrogen, $C_1$–$C_6$ straight chain alkyl, $C_3$–$C_6$ branched chain alkyl, $C_3$–$C_7$ cycloalkyl, phenyl, or —CH$_2$-phenyl;

$R_{13}$ is an amino-protecting group used to transiently protect the moiety NR$_{11}$; or the moiety NR$_{11}$R$_{13}$ may optionally exist as a cyclic imide of the formula:

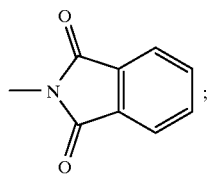

the process comprising converting an amine N-oxide of the formula (II):

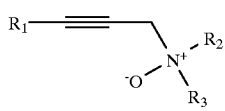
(II)

to the enaminone by treating the amine N-oxide with a hydroxylic solvent.

23. The process of claim 22 wherein —NR$_2$R$_3$ are joined to form a ring of from three to six atoms selected from the group of:

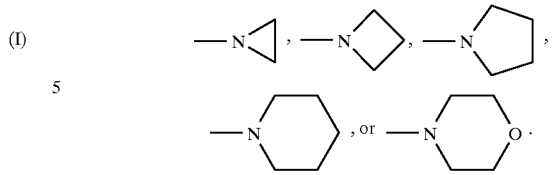

24. The process of claim 22 wherein the amino-protecting group used to transiently protect the moiety NR$_{11}$ is selected from the group of:

(a) the acyl type protective groups formyl, acetyl, chloroacetyl, dichloroacetyl, trichloroacetyl, trifluoroacetyl, phenylacetyl, o-nitrophenoxyacetyl, sec-butyryl, pivaloyl-(also known as tert-butyryl), cyclopropanoyl, benzoyl, o-nitrobenzoyl, α-chlorobutyryl; or (b) the sulfonyl type protecting groups benzenesulfonyl, toluenesulfonyl (tosyl), p-methoxybenzenesulfonyl, trifluoromethylsulfonyl; or (c) the sulfenyl type protecting groups benznesulfenyl, o-nitrobenzenesulfenyl, pentachlorobenzenesulfenyl; or (d) the urethane type protecting groups benzyloxycarbonyl, p-chlorobenzyloxycarbonyl, p-nitrobenzyloxycarbonyl, p-bromobenzyloxycarbonyl, p-methoxybenzyloxycarbonyl, o-nitrobenzyloxycarbonyl, tert-butyloxycarbonyl, tert-amyloxycarbonyl, diisopropylmethoxycarbonyl, isopropyloxycarbonyl, allyloxycarbonyl, cyclopentyloxycarbonyl, adamantyloxycarbonyl, cyclohexyloxycarbonyl, 9-fluorenylmethoxycarbonyl, 2-trimethylsilylethoxycarbonyl.

25. A process for synthesis of enaminones of the formula:

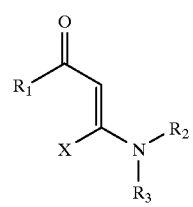
(I)

wherein
X is selected from the group of H, $C_1$–$C_6$ straight chain alkyl, $C_3$–$C_6$ branched chain alkyl, $C_3$–$C_7$ cycloalkyl, phenyl, or —CH$_2$-phenyl;

$R_1$ is selected from the group of hydrogen, $C_1$–$C_6$ straight chain alkyl, $C_3$–$C_6$ branched chain alkyl, $C_3$–$C_7$ cycloalkyl, phenyl, substituted phenyl, —CH$_2$-phenyl, —CH$_2$-substituted phenyl or a group of the formula:

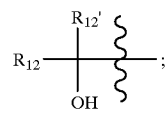

$R_2$ and $R_3$ are independently is selected from the group of $C_1$–$C_6$ straight chain alkyl, $C_3$–$C_6$ branched chain ally, or $C_3$–$C_7$ cycloalkyl; or $R_2$ and $R_3$ may optionally be joined to form a ring of from three to six atoms;

$R_{12}$ and $R_{12'}$ are independently selected from the group of hydrogen, $C_1$–$C_6$ straight chain alkyl, $C_3$–$C_6$ branched chain alkyl, $C_3$–$C_7$ cycloalkyl, phenyl, substituted phenyl, —$CH_2$-phenyl or —$CH_2$-substituted phenyl, the $C_3$–$C_7$ cycloalkyl groups being optionally substituted by from 1 to 3 groups independently selected from $R_5$ to $R_9$;

with a proviso that $R_{12}$ and $R_{12'}$ are not both phenyl or substituted phenyl;

$R_5$–$R_9$ are independently selected from the group of hydrogen, halogen, trifluoromethyl, $C_2$–$C_6$ perfluoroalkyl, $C_1$–$C_6$ straight chain alkyl, $C_3$–$C_6$ branched chain alkyl, $C_3$–$C_7$ cycloalkyl, —CN, —$NO_2$, —$OR_{11}$, —$CO_2R_{11}$, —$NR_{11}R_{13}$, —$NR_{11}C(O)OR_{11'}$, —$NR_{11}C(O)R_{11'}$, —$OC(O)R_{11}$, —$OC(O)OR_{11}$, or —$OC(O)NHR_{11}$;

the process comprising converting an amine N-oxide of the formula (II):

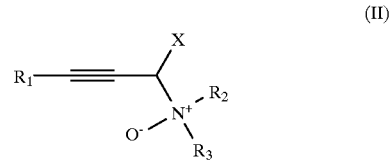

to the enaminone (I) by treating the amine N-oxide (II) with a hydroxylic solvent.

26. The process of claim 25 wherein —$NR_2R_3$ are joined to form a ring of from three to six atoms selected from the group of:

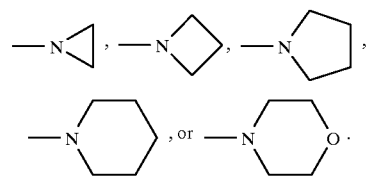

* * * * *